United States Patent
Yoon et al.

(10) Patent No.: US 11,802,106 B2
(45) Date of Patent: Oct. 31, 2023

(54) CATHODE BUFFER LAYER MATERIAL AND ORGANIC OR ORGANIC/INORGANIC HYBRID PHOTOELECTRIC DEVICE COMPRISING SAME

(71) Applicant: KOREA RESEARCH INSTITUTE OF CHEMICAL TECHNOLOGY, Daejeon (KR)

(72) Inventors: Sung Cheol Yoon, Daejeon (KR); Chang Jin Lee, Daejeon (KR); Jaemin Lee, Daejeon (KR); Seung Hun Eom, Daejeon (KR); Seung Hoon Lee, Daejeon (KR); Ju Hyoung Jung, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 436 days.

(21) Appl. No.: 17/059,182

(22) PCT Filed: Apr. 22, 2019

(86) PCT No.: PCT/KR2019/004803
§ 371 (c)(1),
(2) Date: Nov. 25, 2020

(87) PCT Pub. No.: WO2020/017739
PCT Pub. Date: Jan. 23, 2020

(65) Prior Publication Data
US 2021/0198188 A1    Jul. 1, 2021

(30) Foreign Application Priority Data

Jul. 17, 2018   (KR) .................. 10-2018-0082982

(51) Int. Cl.
*C07C 255/04*     (2006.01)
*H10K 30/82*     (2023.01)
(Continued)

(52) U.S. Cl.
CPC ......... *C07C 255/41* (2013.01); *H10K 30/152* (2023.02); *H10K 30/82* (2023.02);
(Continued)

(58) Field of Classification Search
None
See application file for complete search history.

(56) References Cited

U.S. PATENT DOCUMENTS

2014/0202537 A1*   7/2014   Han ................. C09B 23/0058
                                                                                  136/263
2015/0144195 A1*   5/2015   Irwin ................ H01L 51/448
                                                                                  136/260

FOREIGN PATENT DOCUMENTS

KR   10-2015-0115477 A   10/2015
KR       10-1677798 B1   11/2016

OTHER PUBLICATIONS

Kang et al., Dyes and Pigments, No. 149, (2018), pp. 341-347. (Year: 2018).*

(Continued)

*Primary Examiner* — Eli S Mekhlin
(74) *Attorney, Agent, or Firm* — Klarquist Sparkman, LLP

(57) ABSTRACT

The present invention relates to a novel cathode buffer layer material, and an organic or organic/inorganic hybrid photoelectric device comprising same, and, if a novel compound of the present invention is applied to a cathode buffer layer of an organic photoelectric device such as organic solar cells, organic photodiode, colloidal quantum dot solar cell, and perovskite solar cell, a surface property of an electron transfer layer is improved via a high dipole moment of the novel compound, an electron can be easily extracted from a photoactive layer to a cathode electrode, and series resistance and leakage current can be reduced, thereby having a useful industrial effect, as performance of the organic or (Continued)

organic/inorganic hybrid photoelectric device being manufactured, such as an organic solar cell, organic photodiode, colloidal quantum dot solar cell, and perovskite solar cell, can be significantly improved.

5 Claims, 12 Drawing Sheets

(51) Int. Cl.
  H10K 30/15    (2023.01)
  H10K 50/11    (2023.01)
  B82Y 20/00    (2011.01)
  H10K 101/40   (2023.01)
  H10K 101/30   (2023.01)
  H10K 102/10   (2023.01)
  C07C 255/41   (2006.01)

(52) U.S. Cl.
  CPC .............. *H10K 50/11* (2023.02); *B82Y 20/00* (2013.01); *H10K 2101/30* (2023.02); *H10K 2101/40* (2023.02); *H10K 2102/103* (2023.02)

(56) References Cited

OTHER PUBLICATIONS

Author Unknown, "Knoevenagel Condensation: Definitions, Examples and Mechanism" accessed from Chemistry Learner: It's all about Chemistry at https://www.chemistrylearner.com/knoevenagel-condensation.html on Jan. 20, 2022. (Year: 2022).*

Choi et al., "Development of a julolidine-based interfacial modifier for efficient inverted polymer solar cells." *RSC advances* 5, No. 130 (2015): 107540-107546.

International Search Report and Written Opinion mailed in PCT/KR2019/004803, dated Jul. 29, 2019, 9 pages (with English translation of the International Search Report, 2 pages).

Khalaji et al., "Organic compounds containing methoxy and cyanoacrylic acid: Synthesis, characterization, crystal structures, and theoretical studies." *Crystallography Reports* 60, No. 7 (2015): 1019-1026.

Song et al., "Enhanced Performance in Inverted Polymer Solar Cells with D-π-A-Type Molecular Dye Incorporated on ZnO Buffer Layer." *ChemSusChem* 6, No. 8 (2013): 1445-1454.

Zhang et al., "Judicious selection of a pinhole defect filler to generally enhance the performance of organic dye-sensitized solar cells." *Energy & Environmental Science* 6, No. 10 (2013): 2939-2943.

\* cited by examiner

CATHODE BUFFER LAYER MATERIAL AND ORGANIC OR ORGANIC/INORGANIC HYBRID PHOTOELECTRIC DEVICE COMPRISING SAME

CROSS REFERENCE TO RELATED APPLICATIONS

This is the U.S. National Stage of International Application No. PCT/KR2019/004803, filed Apr. 22, 2019, which in turn claims priority of Korean Priority Application No. 10-2018-0082982, filed Jul. 17, 2018, which application is incorporated herein in its entirety.

BACKGROUND OF THE INVENTION

1. Field of the Invention

The present invention relates to a novel cathode buffer layer material, and an organic solar cell, an organic photodiode, a colloidal quantum dot solar cell, a perovskite solar cell, or other organic or organic/inorganic hybrid optoelectronic devices comprising the same.

2. Description of the Related Art

An electronic device has two electrodes and an active layer interposed therebetween as a basic structure. In addition, a typical layer structure is that a charge transport layer is inserted between the electrode or electrodes and the active layer.

At this time, the problem of interlayer adhesion between the active layer and the charge (electron, hole) transport layer or electrode is one of the technical challenges from the beginning of the development of the corresponding devices. This is because interlayer adhesion is as important as the composition of the material of each layer in ensuring the performance of the device.

The easiest approach for interlayer adhesion is to add a third material to a material used as a charge transport layer, such as PEDOT:PSS. For example, the material used as a charge transport layer such as PEDOT:PSS is a charge transport layer material that is used with a polymer such as sulfonated polystyrene, which has conductivity but has a polar functional group as a side chain substituent, and a material used by blending with PEDOT, a compound represented by the general formula of (HO)n-R—(COX)m), for example, a sugar derivative, ethylene glycol, or triethylene glycol.

Another attempt for interlayer adhesion is to interpose a separate adhesive layer in the conventional interlayer construction. For example, in an organic electronic device having a typical layer structure composed of ITO/PEDOT:PSS/P3HT and PCBM/aluminum, an interface layer formed from derivatives of carboxylic anhydrides such as pyromellitic dianhydride and trimellitic anhydride can be inserted between the electrode and the active layer or between the charge transport layer and the active layer.

In addition, in the case of an organic optoelectronic device having an inverted structure suitable for a printing process, a metal ink having large work function such as gold, silver, platinum, etc., is inevitably used as an upper electrode for printing the upper electrode suitable for the printing process. In the conventional structured organic optoelectronic device, the use of aluminum is limited because aluminum is easily oxidized and is not suitable for the printing process. Therefore, in order to lower the high work function of ITO used as a transparent electrode, a thin film such as ZnO or TiO2 is formed on the ITO layer and used. However, these metal oxide-based cathode buffer materials have a problem in that the interface characteristics with the organic photoactive layer are deteriorated and the shunt resistance of the device is reduced, thereby reducing the fill factor (FF) (RSC Adv., 2015, 5, 107540-107546).

In addition, the deterioration of the interfacial characteristics between the inorganic buffer layer and the organic photoactive layer increases the leakage current of the organic photodiode, thereby lowering the detectivity and stability of the device, which delays the commercialization of the organic photodiode device for solution processing.

Thus, the present inventors have tried to solve the problems of the prior art by providing a novel organic material that is easy to control the interface between the metal oxide-based cathode buffer material and the photoactive layer. As a result, the present inventors completed the present invention by finding that the performance of organic or organic/inorganic hybrid optoelectronic devices, for example, organic solar cells, organic photodiodes, colloidal quantum dot solar cells, and perovskite solar cells 1 is excellently improved when the compound of the present invention is used as a cathode buffer layer material.

SUMMARY OF THE INVENTION

It is an object of the present invention to provide a novel cathode buffer layer material.

It is another object of the present invention to provide a preparation method of the novel cathode buffer layer material.

It is another object of the present invention to provide an organic solar cell and an organic photodiode comprising the novel cathode buffer layer material.

It is another object of the present invention to provide an organic or organic/inorganic hybrid optoelectronic device comprising the novel cathode buffer layer material.

To achieve the above objects, in an aspect of the present invention, the present invention provides a compound represented by formula 1 below, or a stereoisomer thereof:

[Formula 1]

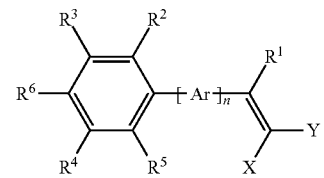

(In formula 1, at least one of X and Y is $CO_2H$, wherein when X is $CO_2H$, Y is hydrogen or CN, and when Y is $CO_2H$, X is hydrogen or CN;

Ar is substituted or unsubstituted $C_{6-10}$ arylene, or substituted or unsubstituted 5 to 10 membered heteroarylene containing at least one hetero atom selected from the group consisting of N, O and S, wherein, the substituted arylene and substituted heteroarylene can be substituted with one or more substituents selected from the group consisting of $C_{1-5}$ straight or branched alkyl, $C_{1-5}$ straight or branched alkoxy;

n is an integer of 0-3;

R[1] is hydrogen, substituted or unsubstituted $C_{1-10}$ straight or branched alkyl, or substituted or unsubstituted $C_{1-10}$ straight or branched alkoxy, wherein, the substituted alkyl and substituted alkoxy can be substituted with one or more substituents selected from the group consisting of $C_{1-5}$ straight or branched alkyl and $C_{1-5}$ straight or branched alkoxy; and R[2], R[3], R[4], R[5], and R[6] are independently H, OH, halogen, substituted or unsubstituted $C_{1-20}$ straight or branched alkyl, substituted or unsubstituted $C_{1-20}$ straight or branched alkoxy, substituted or unsubstituted $C_{2-20}$ straight or branched unsaturated alkyl containing one or more double bonds or triple bonds, wherein, the substituted alkyl, substituted alkoxy and substituted unsaturated alkyl can be substituted with one or more substituents selected from the group consisting of OH, halogen, $C_{1-5}$ straight or branched alkyl, and $C_{1-5}$ straight or branched alkoxy).

In another aspect of the present invention, the present invention provides a preparation method of a compound represented by formula 1 of claim 1 comprising a step of preparing a compound represented by formula 1 from a compound represented by formula 2, as shown in reaction formula 1:

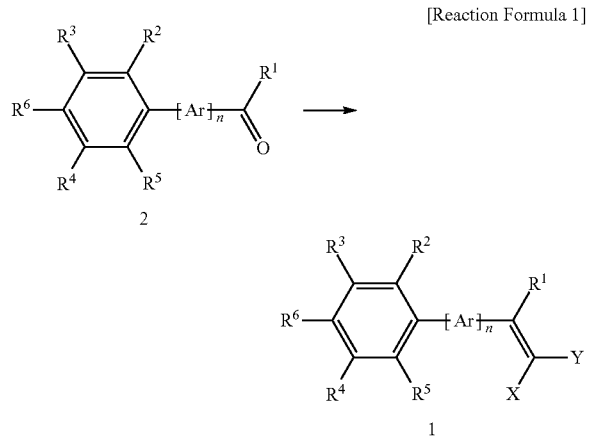

[Reaction Formula 1]

(In reaction formula 1,

X, Y, Ar, n, R[1], R[2], R[3], R[4], R[5], and R[6] are as defined in formula 1).

In another aspect of the present invention, the present invention provides a cathode buffer layer composition comprising the compound represented by formula 1 above, or a stereoisomer thereof.

In another aspect of the present invention, the present invention provides an organic solar cell comprising the cathode buffer layer composition.

In another aspect of the present invention, the present invention provides an organic photodiode comprising the cathode buffer layer composition.

In another aspect of the present invention, the present invention provides a colloidal quantum dot solar cell comprising the cathode buffer layer composition.

In another aspect of the present invention, the present invention provides a perovskite solar cell comprising the cathode buffer layer composition.

In another aspect of the present invention, the present invention provides an organic or organic/inorganic hybrid optoelectronic device comprising the cathode buffer layer composition.

Advantageous Effect

When the novel compound of the present invention is applied to organic optoelectronic devices, for example, cathode buffer layers of organic solar cells, organic photodiodes, colloidal quantum dot solar cells and perovskite solar cells, it is easy to extract electrons from the photoactive layer to the cathode electrode, and has the effect of reducing series resistance and leakage current by improving the surface characteristics of the electron transport layer through the high dipole moment of the novel compound. In addition, the compound of the present invention can significantly improve the performance of organic or organic/inorganic hybrid optoelectronic devices (organic solar cell, organic photodiode, colloidal quantum dot solar cell, perovskite solar cell, etc.), so that it can be industrially useful.

DESCRIPTION OF THE PREFERRED EMBODIMENTS

Figure 1:
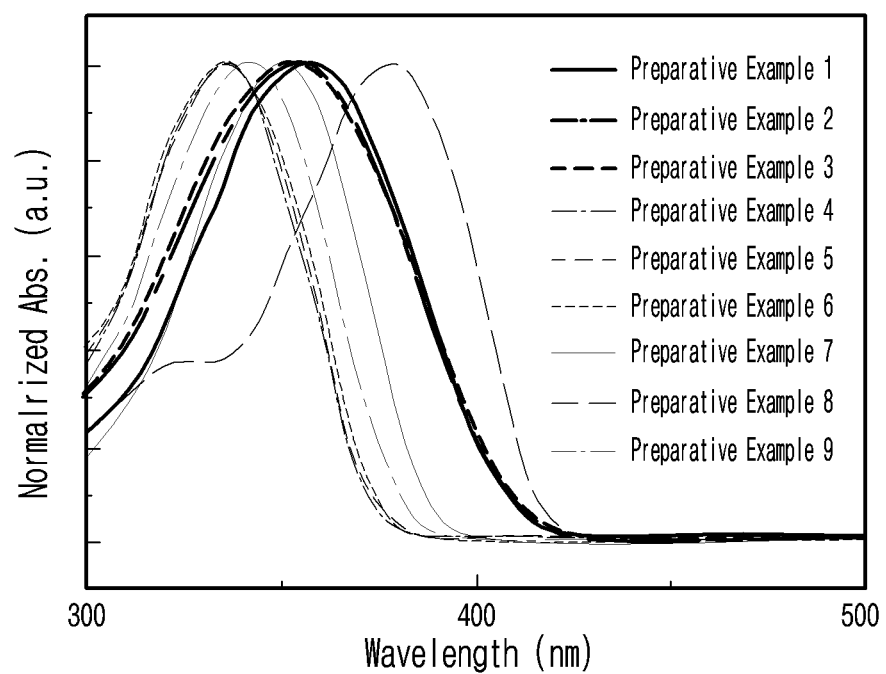
FIG. 1 is a graph showing the UV/Vis absorption spectrum of the compounds of Preparative Examples 1-9.

Hereinafter, the present invention is described in detail.

In an aspect of the present invention, the present invention provides a compound represented by formula 1 below, or a stereoisomer thereof:

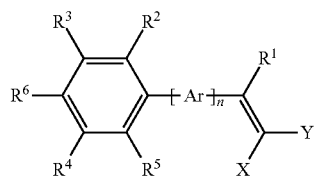

[Formula 1]

(In formula 1, at least one of X and Y is CO$_2$H, wherein when X is CO$_2$H, Y is hydrogen or CN, and when Y is CO$_2$H, X is hydrogen or CN;

Ar is substituted or unsubstituted C$_{6-10}$ arylene, or substituted or unsubstituted 5 to 10 membered heteroarylene containing at least one hetero atom selected from the group consisting of N, O and S, wherein, the substituted arylene and substituted heteroarylene can be substituted with one or more substituents selected from the group consisting of C$_{1-5}$ straight or branched alkyl, C$_{1-5}$ straight or branched alkoxy;

R$^1$ is hydrogen, substituted or unsubstituted C$_{1-10}$ straight or branched alkyl, or substituted or unsubstituted C$_{1-10}$ straight or branched alkoxy, wherein, the substituted alkyl and substituted alkoxy can be substituted with one or more substituents selected from the group consisting of C$_{1-5}$ straight or branched alkyl and C$_{1-5}$ straight or branched alkoxy; and R$^2$, R$^3$, R$^4$, R$^5$, and R$^6$ are independently H, OH, halogen, substituted or unsubstituted C$_{1-20}$ straight or branched alkyl, substituted or unsubstituted C$_{1-20}$ straight or branched alkoxy, substituted or unsubstituted C$_{2-20}$ straight or branched unsaturated alkyl containing one or more double bonds or triple bonds, wherein, the substituted alkyl, substituted alkoxy and substituted unsaturated alkyl can be substituted with one or more substituents selected from the group consisting of OH, halogen, C$_{1-5}$ straight or branched alkyl, and C$_{1-5}$ straight or branched alkoxy).

In an embodiment of the present invention, Ar is substituted or unsubstituted phenylene, wherein the substituted phenylene can be substituted with one or more substituents selected from the group consisting of C$_{1-3}$ straight or branched alkyl and C$_{1-3}$ straight or branched alkoxy.

In another embodiment of the present invention, n can be an integer of 0 or 1.

In another embodiment of the present invention, R$^1$ is hydrogen or methyl, and R$^2$, R$^3$, R$^4$, R$^5$ and R$^6$ can be independently H, or unsubstituted C$_{1-20}$ straight or branched alkoxy.

In an embodiment of the present invention, the compound represented by formula 1 can be any compound selected from the group consisting of the following compounds, or a stereoisomer thereof:

(1) 2-cyano-3-(4'-methoxybiphenyl-4-yl)acrylic acid;
(2) 2-cyano-3-(4'-ethoxybiphenyl-4-yl)acrylic acid;
(3) 3-(4'-butoxybiphenyl-4-yl)-2-cyanoacrylic acid;
(4) 2-cyano-3-(4-methoxyphenyl)acrylic acid;
(5) 2-cyano-3-(4-ethoxyphenyl)acrylic acid;
(6) 3-(4-butoxyphenyl)-2-cyanoacrylic acid;
(7) 2-cyano-3-(4-(hexyloxy)phenyl)acrylic acid;
(8) 3-(2,4-bis(hexyloxy)phenyl)-2-cyanoacrylic acid; and
(9) 2-cyano-3-(3,5-dimethoxyphenyl)acrylic acid.

In an aspect of the present invention, the compound represented by formula 1 or a stereoisomer thereof is a molecular sieve having a large dipole moment, and the alkoxy phenyl moiety and the cyanoacrylic acid moiety, which are each terminal region of the compound, are a hydrophobic donor and a hydrophilic acceptor, respectively.

The compound of the present invention, or a stereoisomer thereof can form a double layer with a photoactive layer and an existing metal oxide-based cathode buffer, or can be dispersed in an existing metal oxide-based cathode buffer material, and in particular, can form a high dipole moment layer at the interface, so that the electrons generated in the photoactive layer can be easily transferred to the cathode electrode.

In addition, the compound of the present invention, or a stereoisomer thereof can be used as a composition for a cathode buffer layer, and can be applied to organic optoelectronic devices, for example, cathode buffer layers of organic solar cells, organic photodiodes, colloidal quantum dot solar cells and perovskite solar cells. From this, it shows surprising effects such as improvement in device efficiency and device stability.

In an embodiment of the present invention, the organic solar cell devices of Examples 1-11, prepared by applying the compounds of Preparative Examples 1-9, contained PV-D4610 (Merck's donor polymer), PTB7-Th:PC70BM or PPDT2FBT:PC70BM as a photoactive layer, but not always limited thereto. ZnO was used as a cathode buffer material, and one layer was formed between the two layers by one method to form a cathode buffer layer with a double layer in the form of ZnO/the compound of the present invention. Alternatively, after mixing with a cathode buffer material, this solution was deposited to form a single cathode buffer layer, which could be applied to an organic solar cell device.

In another embodiment of the present invention, the colloidal quantum dot solar cell devices of Examples 12-14, prepared by applying the compounds of Preparative Examples 1-9 of the present invention, contained PbS-PDMII:PbS-PDT as a photoactive layer, but not always limited thereto. ZnO was used as a cathode buffer material, and one layer was formed between the two layers by one method to form a cathode buffer layer with a double layer in the form of ZnO/the compound of the present invention, which could be applied to a colloidal quantum dot solar cell device.

In another embodiment of the present invention, the perovskite solar cell device of Example 15, prepared by applying the compounds of Preparative Examples 1-9 of the present invention, contained a perovskite layer with PbI$_2$ and methylammonium iodide as a photoactive layer, but not always limited thereto. ZnO was used as a cathode buffer material, and one layer was formed between the two layers by one method to form a cathode buffer layer with a double layer in the form of ZnO/the compound of the present invention, which could be applied to a perovskite solar cell device.

In another aspect of the present invention, when the organic or organic/inorganic hybrid optoelectronic device is manufactured by the preparation method with a single cathode buffer layer, an effect of remarkable improvement in device efficiency and stability can be exhibited compared to the preparation method with a double layer. In addition, the preparation method with a single layer has an advantage that can be more easily applied to a device manufacturing process through a printing method than the preparation method with a double layer.

On the other hand, in an embodiment of the present invention, the dipole moment of the molecular sieves of the compounds of Preparative Examples 1-9 was calculated by DFT (Density Functional Theory, B3LYP, 6-31G*) method using Spartan 16 software. As a result, the molecular sieves of the compounds of Preparative Examples 1-9 of the present invention had 8-11 debye dipole moment. Therefore, the electron transport from the photoactive layer to the cathode electrode can be performed better. In particular, the compounds of Preparative Examples 1-9 of the present invention have an implied molecular sieve structure, which is more advantageous in electron transport.

In another aspect of the present invention, the present invention provides a preparation method of a compound represented by formula 1 of claim 1 comprising a step of preparing a compound represented by formula 1 from a compound represented by formula 2, as shown in reaction formula 1:

[Reaction Formula 1]

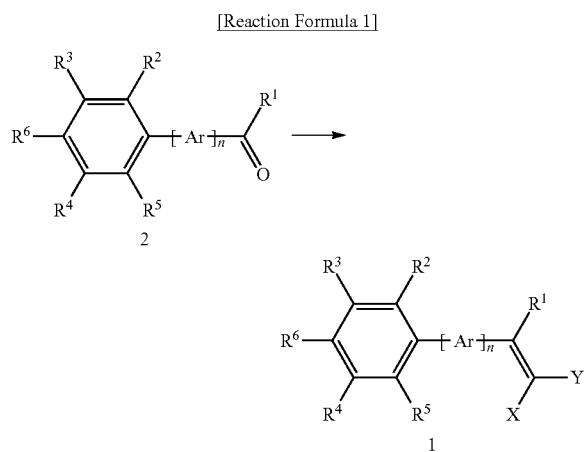

(In reaction formula 1,

X, Y, Ar, n, $R^1$, $R^2$, $R^3$, $R^4$, $R^5$, and $R^6$ are as defined in formula 1).

Hereinafter, the preparation method of a compound represented by formula 1 is described in more detail step by step.

In the preparation method of a compound represented by formula 1 according to the present invention, it is understood that prior to the step of preparing a compound represented by formula 1 from a compound represented by formula 2, the reaction of introducing an aldehyde group into phenyl is preceded so that a cyanoacrylic acid part, which is a hydrophilic acceptor moiety, can be introduced into a hydrophobic donor moiety.

In an aspect of the present invention, a compound represented by formula 2, an aldehyde derivative, can be prepared by reacting with $POCl_3$. Herein, the available solvent is not particularly limited, but one selected from the group consisting of diethyl ether, toluene, dimethyl formamide (DMF), tetrahydrofuran (THF), dichloromethane (DCM) and acetonitrile, or a mixture of two or more solvents can be used. In an embodiment of the present invention, DMF can be used.

In addition, the reaction time of the step is not particularly limited as long as the product can be obtained, but the reaction can be performed for 5 to 40 hours, 10 to 30 hours, 20 to 30 hours, or about 24 hours.

Further, the reaction temperature of the step is not particularly limited, but the reaction can be performed at 60 to 90° C., 70 to 90° C., or about 80 to 85° C.

In particular, the compound represented by formula 1 of the present invention, or a stereoisomer thereof acts at the interface between the cathode buffer material and the photoactive layer so that electrons can be more easily transferred from the photoactive layer to the cathode electrode by modifying the cathode buffer material. In consideration of this, if any one of the effects desired in the present invention, such as the effect of facilitating electron transport; the effect of improving the efficiency of organic optoelectronic devices, for example, organic solar cells, organic photodiodes, colloidal quantum dot solar cells and perovskite solar cells; the effect of reducing series resistance and leakage current; the effect of improving photoelectric conversion efficiency; and the effect of improving device stability, is exhibited by applying the compound of the present invention or its stereoisomer, it is included in the cathode material, and this is also included in the scope of the present invention.

In the preparation method of a compound represented by formula 1 according to the present invention, the step of preparing a compound represented by formula 1 from a compound represented by formula 2 is a step of preparing a cathode buffer layer modification compound, the final target compound represented by formula 1, by introducing a hydrophilic acceptor moiety, which is an acrylic acid derivative, into an aldehyde group substitution part of the compound represented by formula 2.

In an aspect of the above step, the compound represented by formula 2 is reacted with, for example, carboxylic acid such as cyanoacetic acid or malonic acid, to which piperidine is added.

Herein, the available solvent is not particularly limited, but one selected from the group consisting of CAN (acetonitrile), chloroform, dimethyl formamide (DMF), tetrahydrofuran (THF), and dimethyl sulfoxide (DMSO), or a mixture of two or more solvents can be used. In an embodiment of the present invention, a mixed solvent of acetonitrile and chloroform can be used.

In addition, the reaction time of the step is not particularly limited as long as the product can be obtained, but the reaction can be performed for 5 to 40 hours, 10 to 30 hours, 12 to 24 hours, or 8 to 20 hours.

Further, the reaction temperature of the step is not particularly limited, but the reaction can be performed at 60 to 90° C., 70 to 90° C., or about 80 to 85° C.

The preparation method described hereinbefore can be understood to be the preparation method of an embodiment of the present invention, and in consideration of the structure of the target compound and the yield of the product, the reaction conditions can be changed, and the above-mentioned preparation method can be modified.

The objects of the present invention are to provide a compound represented by formula 1, and to improve the efficiency and stability of organic or organic/inorganic hybrid optoelectronic devices using the same. Thus, it should be understood that any preparation method in which the compound of formula 1 to be provided by the present invention can be prepared by the above-mentioned preparation method is included in the scope of the present invention without limitation.

In another aspect of the present invention, the present invention provides a composition for a cathode buffer layer comprising the compound represented by formula 1, or the stereoisomer thereof.

At this time, the composition for a cathode buffer layer can be understood to include the compound represented by formula 1 as a main component, and can include additional methods and components for increasing charge transport or increasing electron transfer between the cathode electrode and the photoactive layer.

In particular, in an aspect of the present invention, the composition for a cathode buffer layer can be understood to include the compound represented by formula 1 of the present invention and a cathode buffer material.

Herein, the cathode buffer material can be at least one cathode buffer material selected from the group consisting of n-type metal oxides, transition metal chelates and alkali metal compounds. In an embodiment of the present invention, the cathode buffer material can be one or more selected from the group consisting of ZnO, TiOx, titanium chelate, zirconium chelate, LiF, CsF and Cs2CO3, and if it is known as a conventional cathode buffer material, this can be included in the present invention without limitation.

In particular, the compound represented by formula 1 of the present invention, or a stereoisomer thereof acts at the interface between the cathode buffer material and the photoactive layer so that electrons can be more easily transferred from the photoactive layer to the cathode electrode by modifying the cathode buffer material. In consideration of this, if any one of the effects desired in the present invention, such as the effect of facilitating electron transport; the effect of improving the efficiency of organic optoelectronic devices, for example, organic solar cells, organic photodiodes, colloidal quantum dot solar cells and perovskite solar cells; the effect of reducing series resistance and leakage current; the effect of improving photoelectric conversion efficiency; and the effect of improving device stability, is exhibited by applying the compound of the present invention or its stereoisomer, it is included in the cathode material, and this is also included in the scope of the present invention.

In an aspect of the present invention, the present invention provides a preparation method of a composition for a cathode buffer layer comprising a step of preparing a mixed solution by mixing a compound represented by formula 1 or a stereoisomer thereof with a cathode buffer material.

Herein, the cathode buffer material refers to the cathode buffer material described above, and in preparing the composition, it is prepared as a solution, for example, a mixed solution prepared as a sol-gel solution.

In the following experimental examples of the present invention, in particular, in preparing a cathode buffer layer, the cathode buffer material, the compound of the present invention, and the stereoisomer thereof are separately formed and provided as a double layer. Alternatively, after mixing them as described above, a cathode buffer layer is provided by forming a film.

Herein, if the method is a method in which the desired effect of the present invention is exhibited, it is included in the scope of the present invention, regardless of the method of preparing a double layer or a single layer after mixing. As a specific example, in the following experimental example, it was experimentally proved that the most improved organic solar cell efficiency was exhibited in the example of mixing the cathode buffer material and the compound of the present invention before the cathode buffer layer formation. By forming a cathode buffer layer as a single layer after mixing, a more excellent effect can be achieved in organic or organic/inorganic hybrid optoelectronic devices, for example, solar cells.

In addition, compared to the method of preparing a cathode buffer layer as a double layer, the method of forming a film as a single layer after mixing can reduce and simplify the steps of the manufacturing process, in terms of manufacturing organic or organic/inorganic hybrid optoelectronic devices by the printing process, thereby providing excellent advantages in terms of the process.

In another aspect of the present invention, the present invention provides a cathode buffer layer comprising a compound represented by formula 1, or a stereoisomer thereof; and one or more cathode buffer materials selected from the group consisting of n-type metal oxides, transition metal chelates, and alkali metal compounds.

At this time, if the cathode buffer material is the same as the cathode buffer material described in the preparation method of a composition for a cathode buffer layer, for example, if it is used for the cathode buffer layer provided between the photoactive layer and the cathode electrode of an organic or organic/inorganic hybrid photoelectric device, it is included in the present invention without limitation.

On the other hand, the compound represented by formula 1 of the present invention or the stereoisomer thereof can be mixed and dispersed in the cathode buffer material to form a single layer. Alternatively, the compound represented by formula 1 of the present invention or the stereoisomer thereof can be formed as a double layer as a separate layer with a first layer comprising the cathode material and a second layer comprising the compound of formula 1 or a stereoisomer thereof.

In particular, in an aspect of the present invention, the cathode buffer layer can be applied to organic or organic/inorganic hybrid photovoltaic devices such as organic solar cells, organic photodiodes, colloidal quantum dot solar cells and perovskite solar cells, and other examples, inverted structure organic or organic/inorganic hybrid photoelectric devices such as reverse structure organic solar cell, organic photodiode, colloidal quantum dot solar cell and perovskite solar cell, etc. Due to the dipole moment caused by the molecular sieve structure of the compound of formula 1 or its stereoisomer of the present invention, an effect of excellently improving performance or characteristics such as efficiency, stability, and the like of the device can be finally achieved.

In another aspect of the present invention, the present invention provides an organic or organic/inorganic hybrid photoelectric device comprising a first electrode; a second electrode provided opposite to the first electrode; a photoactive layer provided between the first electrode and the second electrode; and a cathode buffer layer of claim 7 provided between the photoactive layer and the first electrode or the second electrode.

In another aspect of the present invention, the present invention provides an organic or organic/inorganic hybrid photoelectric device comprising the composition for a cathode buffer layer.

In an aspect of the present invention, it can be understood that one of the first electrode and the second electrode is an anode electrode and the other is a cathode electrode.

In an aspect of the present invention, the organic or organic/inorganic hybrid photoelectric device (organic solar cell, organic photodiode, colloidal quantum dot solar cell, perovskite solar cell, etc.) can further include a substrate, a hole transport layer and/or an electron transport layer.

In an embodiment of the present invention, the photoactive layer includes a hole transport layer, a hole injection layer or a hole transport/injection layer.

In another embodiment of the present invention, the photoactive layer includes a hole injection layer, a hole transport layer or a hole transport/injection layer.

In an embodiment of the present invention, electrons and holes are generated between the electron donor and the electron acceptor when the organic or organic/inorganic hybrid optoelectronic device receives photons from an external light source. The generated holes are transported to the anode through the electron donor layer.

In an embodiment of the present invention, the organic or organic/inorganic hybrid optoelectronic device can further include one or two or more photoactive layers selected from the group consisting of a hole injection layer, a hole transport layer, a hole blocking layer, a charge generation layer, an electron blocking layer, an electron injection layer, and an electron transport layer.

In an embodiment of the present invention, the organic or organic/inorganic hybrid photoelectric device can be arranged in the order of a cathode, a photoactive layer and an anode, or can be arranged in the order of an anode, a photoactive layer and a cathode, but not always limited thereto.

In another embodiment of the present invention, the organic or organic/inorganic hybrid photoelectric device can be arranged in the order of an anode, a hole transport layer, a photoactive layer, an electron transport layer and a cathode, or can be arranged in the order of a cathode, an electron transport layer, a photoactive layer, a hole transport layer and an anode, but not always limited thereto.

In another embodiment of the present invention, the cathode buffer layer can be provided between the photoactive layer and the hole transport layer or between the photoactive layer and the electron transport layer. At this time, a hole injection layer can be further provided between the anode and the hole transport layer. In addition, an electron injection layer can be further provided between the cathode and the electron transport layer.

In an embodiment of the present invention, the photoactive layer includes one or two or more selected from the group consisting of electron donors and acceptors.

In an embodiment of the present invention, the electron acceptor material can be selected from the group consisting of fullerene, fullerene derivatives, vasocuproin, semiconducting elements, semiconducting compounds and combinations thereof. Specifically, it can be PC61BM (phenyl C61-butyric acid methyl ester) or PC71BM (phenyl C71-butyric acid methyl ester).

In an embodiment of the present invention, the electron donor and electron acceptor constitute a bulk heterojunction (BHJ). The electron donor material and the electron acceptor material can be mixed in the ratio of 1:10 to 10:1 (w/w).

In an embodiment of the present invention, the photoactive layer can have a bilayer structure including an n-type photoactive layer and a p-type photoactive layer.

In the present invention, the substrate can be a glass substrate or a transparent plastic substrate having excellent transparency, surface smoothness, ease of handling, and waterproofness, but not always limited thereto, and the substrate is not limited as long as it is a substrate generally used for organic or organic/inorganic hybrid photoelectric devices. Particularly, the substrate includes glass or PET (polyethylene terephthalate), PEN (polyethylene naphthalate), PP (polypropylene), PI (polyimide), TAC (triacetyl cellulose), and the like, but not always limited thereto.

The anode electrode can be a transparent material with excellent conductivity, but not always limited thereto. Examples of the anode electrode include metals such as vanadium, chromium, copper, zinc and gold, or alloys thereof; metal oxides such as zinc oxide, indium oxide, indium tin oxide (ITO) and indium zinc oxide (IZO); combination of metal and oxide such as $ZnO:Al$ or $SNO2:Sb$; conductive polymers such as poly(3-methylthiophene), poly [3,4-(ethylene-1,2-dioxy)thiophene] (PEDOT), polypyrrole and polyaniline, but not always limited thereto.

The anode electrode can be formed by applying to one surface of a substrate or coating in a film form using sputtering, E-beam, thermal evaporation, spin coating, screen printing, inkjet printing, doctor blade or gravure printing method.

When the anode electrode is formed on a substrate, it may undergo cleaning, moisture removal, and hydrophilicity modification processes.

For example, a patterned ITO substrate is sequentially cleaned with a cleaning agent, acetone, and isopropyl alcohol (IPA), and then dried on a hot plate at 100 to 150° C. for 1 to 30 minutes, preferably at 120° C. for 10 minutes to remove moisture. When the substrate is completely cleaned, the substrate surface is modified to be hydrophilic.

Through the surface modification as described above, the bonding surface potential can be maintained at a level suitable for the surface potential of the photoactive layer. In addition, the formation of a polymer thin film on the anode electrode is facilitated through the modification, and the quality of the thin film can be improved.

The pretreatment technology for the anode electrode includes a) surface oxidation using parallel plate type discharge, b) surface oxidation through ozone generated using UV in vacuo, and c) oxidation using oxygen radicals generated by plasma.

One of the above methods can be selected according to the state of the anode electrode or the substrate. However, regardless of which method is used, it is generally preferable to prevent the oxygen from leaving the anode electrode or the surface of the substrate and to minimize the residual moisture and organic matter.

As a specific example, a method of oxidizing the surface through ozone generated using UV can be used.

At this time, after ultrasonic cleaning, the patterned ITO substrate is baked on a hot plate, dried well, and then put into a chamber. By operating a UV lamp, the patterned ITO substrate can be cleaned by ozone generated when oxygen gas reacts with UV light.

However, the method of modifying the surface of the patterned ITO substrate in the present invention is not particularly limited, and any method can be used as long as it is a method of oxidizing the substrate.

The cathode electrode can be a metal having a small work function, but not always limited thereto. Particularly, the electrode can be a metal such as magnesium, calcium, sodium, potassium, titanium, indium, yttrium, lithium, gadolinium, aluminum, silver, tin and lead, or an alloy thereof; or a material having a multilayer structure such as LiF/Al, LiO$_2$/Al, LiF/Fe, Al:Li, Al:BaF$_2$ and Al:BaF$_2$:Ba, but not always limited thereto.

The cathode electrode can be formed by depositing inside a thermal evaporator showing the degree of vacuum of 5×10$^{-7}$ torr or less, but not always limited thereto.

The material of the hole transport layer and/or the electron transport layer plays a role of efficiently transferring the electrons and holes separated in the photoactive layer to the electrode, but the material is not particularly limited.

The hole transport layer material can be PEDOT:PSS (Poly(3,4-ethylenediocythiophene) doped with poly(styrenesulfonic acid)), molybdenum oxide (MoOx); vanadium oxide (V205); nickel oxide (NiO); and tungsten oxide (WOx), but not always limited thereto.

The electron transport layer material can be electron-extracting metal oxide, and particularly, a metal complex of 8-hydroxyquinoline; a complex containing Alq$_3$; a metal complex containing Liq; LiF; Ca; titanium oxide (TiOx); zinc oxide (ZnO); and cesium carbonate (Cs$_2$CO$_3$), but not always limited thereto.

The photoactive layer can be formed by dissolving a photoactive material such as an electron donor and/or an electron acceptor in an organic solvent using spin coating, dip coating, screen printing, spray coating, doctor blade, brush painting, etc., but not always limited thereto.

In an aspect of the present invention, any one of the first electrode or the second electrode can be an ITO electrode, and the other can be MoO$_3$/Ag.

In an aspect of the present invention, when the composition for a cathode buffer layer of the present invention is used in preparing an organic solar cell, a colloidal quantum dot solar cell or a perovskite solar cell, electron transfer between the photoactive layer and the cathode electrode is significantly improved. In addition, the photoelectric conversion efficiency (PCE) of an organic solar cell, a colloidal quantum dot solar cell or a perovskite solar cell can be significantly improved to 8% or more, or 9% or more. Therefore, it can be used as an effective method for improving the efficiency of an organic solar cell, a colloidal quantum dot solar cell or a perovskite solar cell in the art.

In particular, the organic/inorganic hybrid material has the advantages of organic materials that have low manufacturing cost, simple manufacturing and device preparing processes, and easy to control optical and electrical properties, as well as inorganic materials that have high charge mobility and mechanical/thermal stability, so that it has been in the spotlight academically and industrially. Since the organic/inorganic hybrid photoelectric device comprising the novel cathode buffer layer material provided herein has the above advantages, it can meet the needs of the art.

On the other hand, the organic/inorganic hybrid perovskite material has high color purity, easy color control, and low synthesis cost, and thus has a great potential for development as a luminous material. The hybrid material has a layered structure in which the 2D plane of an inorganic material is sandwiched between the 2D plane of an organic material, and the difference in permittivity between the inorganic material and the organic material is large (εorganic≈2.4, εinorganic≈6.1). Accordingly, excitons are bound to the inorganic layer, and thus the material is formed to have high color purity (Full width at half maximum (FWHM) 20 nm).

For example, in the organic/inorganic hybrid perovskite, organic ammonium (RNH$_3$) cations are located at A site and halides (Cl, Br, I) are located at X site in ABX3 structure to form an organometallic halide perovskite material.

On the other hand, the organic/inorganic hybrid perovskite (or organometallic halide perovskite) is similar to the lamellar structure because the organic plane (or alkali metal plane) and the inorganic plane are alternately stacked, so that excitons can be bound within the inorganic plane. Essentially, it can be an ideal illuminant that emits light of very high color purity due to the crystal structure itself rather than the size of the material.

In an aspect of the present invention, when the cathode buffer composition of the present invention is used to prepare an organic photodiode, leakage current is significantly reduced. In addition, the leakage current of the organic photodiode can be reduced to 10$^{-9}$ A/cm$^2$ or less under the condition of applying a reverse voltage of −2V. Therefore, it can be used as an effective method for improving the detectivity of an organic photodiode in the art.

In addition, the present invention provides a preparation method of an organic solar cell, a colloidal quantum dot solar cell or a perovskite solar cell comprising the following steps:

preparing a mixed solution by mixing the compound represented by formula 1 or the stereoisomer thereof with a cathode buffer material; and forming a film of the mixed solution.

In the preparation method of an organic solar cell, a colloidal quantum dot solar cell or a perovskite solar cell, the step of preparing a mixed solution by mixing the compound represented by formula 1 or the stereoisomer thereof with a cathode buffer material is a step of mixing the cathode buffer material and the compounds of Preparative Examples 1-9 in a single layer instead of a double layer, based on the device characteristic values measured from the organic solar cell devices of Examples 1-10, the organic photodiode device of Example 11, the colloidal quantum dot solar cells of Examples 12-14 and the perovskite solar cell of Example 15. It should be understood that the device prepared by the method is a specific example presented from the achievement of superior organic solar cell, colloidal quantum dot solar cell and perovskite solar cell characteristics.

In the present invention, in addition to the preparation method of the above-mentioned mixed solution, a layer was formed only with a cathode material, and a modified layer including the compound represented by formula 1 and the stereoisomer thereof was separately prepared, and a bilayer was prepared, which is shown in Examples 1-8 and 12-15.

In particular, the organic solar cell, the colloidal quantum dot solar cell, and the perovskite solar cell prepared by the above method have also been shown as experimental examples to achieve excellent device characteristics.

Therefore, the preparation method of an organic solar cell, a colloidal quantum dot solar cell or a perovskite solar cell of the present invention includes the step of preparing a double layer. Furthermore, the present invention relates to the formula 1 or a stereoisomer thereof in the organic solar cell. As long as it includes the step of incorporating as part of the battery, it can be understood to be the method of manufacturing the present invention. Furthermore, as long as a method includes the step of including the compound of formula 1 or the stereoisomer thereof of the present invention as a part of the organic solar cell, it can be understood that it is the preparation method of the present invention.

However, the step of preparing a mixed solution is a method of manufacturing an organic solar cell, a colloidal quantum dot solar cell, or a perovskite solar cell device in which a more excellent effect is achieved, and is included as an aspect of the present invention.

In the preparation method of an organic solar cell, a colloidal quantum dot solar cell or a perovskite solar cell, the step of forming a film of the mixed solution can be understood to be a step of forming a film as a cathode buffer layer, and is not particularly limited, but in an aspect of the present invention, it can be understood to include all kinds of conventionally used film forming methods.

Using the compounds of Preparative Examples 1-9, the organic solar cell devices of Examples 1-10, the organic photodiode device of Example 11, the colloidal quantum dot solar cell devices of Example 12-14 and the perovskite solar cell of Example 15 were prepared, and the photovoltaic properties were tested and evaluated in order to experimentally measure the energy conversion efficiency of an organic or organic/inorganic hybrid photoelectric device, that is a photoelectric conversion device such as an organic solar cell, an organic photodiode, a colloidal quantum dot solar cell and a perovskite solar cell device prepared using the composition for a cathode buffer layer comprising the compound represented by formula 1 of the present invention. Since the compound represented by formula 1 of the present invention or the stereoisomer thereof is a molecular sieve having a high dipole moment, it facilitates electron transfer between the photoactive layer and the cathode electrode layer, thereby providing remarkably high short circuit current (Jsc) and fill factor (FF). In conclusion, it was confirmed that Voc, Jsc, and FF, which are factors that determine the device performance of an organic solar cell, were all increased, resulting in remarkably high power conversion efficiency (PCE).

Hereinafter, the present invention will be described in detail by the following preparative examples, examples and experimental examples.

However, the following preparative examples and examples are only for illustrating the present invention, and the contents of the present invention are not limited thereto.

<Preparative Example 1> Preparation of 2-cyano-3-(4'-methoxybiphenyl-4-yl)acrylic acid

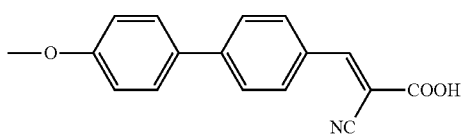 [SMILES: COc1ccc(-c2ccc(/C=C(\C#N)C(=O)O)cc2)cc1]

Step 1. Preparation of 4'-methoxy-[1,1'-biphenyl]-4-carbaldehyde

1-Bromo-4-methoxybenzene (3 g, 16.04 mmol), 4-(4,4,5,5-tetramethyl-1,3,2-dioxaborolan-2-yl)-benzaldehyde (5.85 g, 24.06 mmol) and Pd(PPh$_3$)$_4$ (0.734 g, 0.80 mmol) were dissolved in toluene (50 mL) under nitrogen, to which 3 mL of 2 M K$_2$CO$_3$ was added, followed by stirring at 110° C. for 24 hours. Upon completion of the reaction, the reactant was extracted with MC and water. The organic layer was dried over MgSO$_4$ and filtered. After removing the solvent from the filtrate, it was purified through a column (MC:n-hexane=1:4) to give a target compound (50%).

$^1$H NMR (400 MHz, CDCl$_3$) δ10.04 (s, 1H), 7.93 (d, J=8.4 Hz, 2H), 7.72 (d, J=8.2 Hz, 2H), 7.62-7.52 (m, 2H), 7.01 (d, J=8.8 Hz, 2H), 3.87 (s, 3H).

Step 2. Preparation of (Z)-2-cyano-3-(4'-methoxyl-[1,1'-biphenyl]-4-yl)acrylic acid The compound prepared in step 1 (0.51 g, 2.40 mmol) and cyanoacetic acid (0.46 g, 5.41 mmol) were dissolved in ACN (20 mL) under nitrogen, to which piperidine (0.24 mL, 2.40 mmol) was added, followed by stirring at 80° C. for 24 hours. Upon completion of the reaction, a solid was precipitated with HCl solution. The precipitated solid was filtered and dried to give a target compound (44.8%).

$^1$H NMR (400 MHz, DMSO-d6) δ8.36 (s, 1H), 8.12 (d, J=8.4 Hz, 2H), 7.88 (d, J=8.4 Hz, 2H), 7.77 (d, J=8.8 Hz, 2H), 7.07 (d, J=8.8 Hz, 2H), 3.82 (s, 3H).

<Preparative Example 2> Preparation of 2-cyano-3-(4'-ethoxybiphenyl-4-yl)acrylic acid

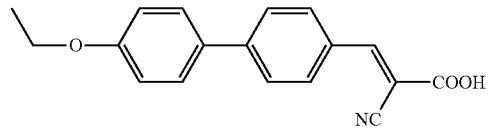 [SMILES: CCOc1ccc(-c2ccc(/C=C(\C#N)C(=O)O)cc2)cc1]

A target compound (71%) was prepared in the same manner as described in Preparative Example 1, except that 1-bromo-4-ethoxybenzene was used instead of 1-bromo-4-methoxybenzene used in Preparative Example 1.

$^1$H NMR (400 MHz, DMSO-d$_6$) δ8.35 (s, 1H), 8.12 (d, J=8.5 Hz, 2H), 7.87 (d, J=8.5 Hz, 2H), 7.75 (d, J=8.8 Hz, 2H), 7.05 (d, J=8.8 Hz, 2H), 4.10 (q, J=7.0 Hz, 2H), 1.36 (t, J=7.0 Hz, 3H).

<Preparative Example 3> Preparation of 3-(4'-butoxybiphenyl-4-yl)-2-cyanoacrylic acid

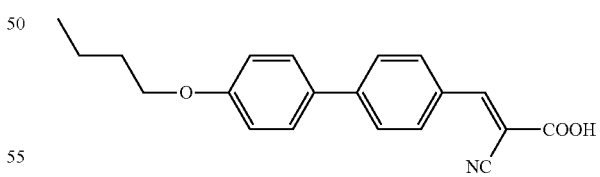

A target compound (85.5%) was prepared in the same manner as described in Preparative Example 1, except that 1-bromo-4-n-butoxybenzene was used instead of 1-bromo-4-methoxybenzene used in Preparative Example 1.

$^1$H NMR (400 MHz, CDCl$_3$) δ 8.32 (s, 1H), 8.10 (d, J=8.4 Hz, 2H), 7.72 (d, J=8.5 Hz, 2H), 7.60 (d, J=8.8 Hz, 2H), 7.01 (d, J=8.9 Hz, 2H), 4.03 (t, J=6.5 Hz, 2H), 1.92-1.62 (m, 2H), 1.62-1.43 (m, 2H), 1.00 (t, J=7.4 Hz, 3H).

<Preparative Example 4> Preparation of 2-cyano-3-(4-methoxyphenyl)acrylic acid

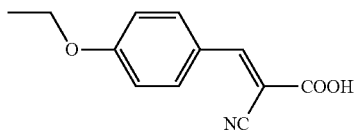

4-Methoxybenzaldehyde (5 g, 36.72 mmol) and cyanoacetic acid (4.69 g, 55.08 mmol) were dissolved in ACN (50 mL) under nitrogen, to which piperidine (3.6 mL, 36.72 mmol) was added, followed by stirring at 80° C. for 24 hours. Upon completion of the reaction, a solid was precipitated with HCl solution. The precipitated solid was filtered and dried to give a target compound (73%).

$^1$H NMR (400 MHz, DMSO-$d_6$) δ 8.27 (s, 1H), 8.07 (d, J=8.8 Hz, 2H), 7.15 (d, J=8.9 Hz, 2H), 3.87 (s, 3H).

<Preparative Example 5> Preparation of 2-cyano-3-(4-ethoxyphenyl)acrylic acid

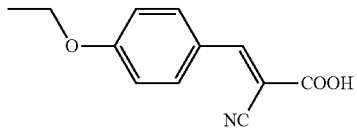 [SMILES: CCOc1ccc(/C=C(\C#N)C(=O)O)cc1]

A target compound (80%) was prepared in the same manner as described in Preparative Example 4, except that 4-ethoxybenzaldehyde was used instead of 4-methoxybenzaldehyde used in Preparative Example 4.

$^1$H NMR (400 MHz, DMSO-$d_6$) δ 8.26 (s, 1H), 8.06 (d, J=8.9 Hz, 2H), 7.13 (d, J=8.9 Hz, 2H), 4.15 (t, J=7.0 Hz, 2H), 1.36 (t, J=7.0 Hz, 3H).

<Preparative Example 6> Preparation of 3-(4-butoxyphenyl)-2-cyanoacrylic acid

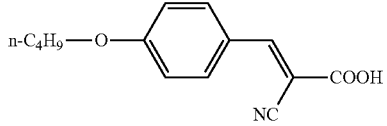

A target compound (80%) was prepared in the same manner as described in Preparative Example 4, except that 4-n-butoxybenzaldehyde was used instead of 4-methoxybenzaldehyde used in Preparative Example 4.

$^1$H NMR (400 MHz, CDCl$_3$) δ 8.24 (s, 1H), 8.04 (d, J=8.9 Hz, 2H), 7.00 (d, J=8.9 Hz, 2H), 4.07 (t, J=6.5 Hz, 2H), 1.94-1.68 (m, 2H), 1.51 (m, J=15.0, 7.5 Hz, 2H), 0.99 (t, J=7.4 Hz, 3H).

<Preparative Example 7> Preparation of 2-cyano-3-(4-(hexyloxy)phenyl)acrylic acid

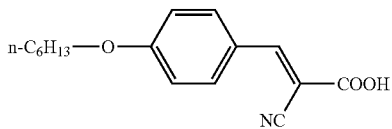

A target compound (20%) was prepared in the same manner as described in Preparative Example 4, except that 4-n-hexyloxybenzaldehyde was used instead of 4-methoxybenzaldehyde used in Preparative Example 4.

$^1$H NMR (400 MHz, DMSO-$d_6$) δ 8.25 (s, 1H), 8.05 (d, J=8.9 Hz, 2H), 7.14 (d, J=8.9 Hz, 2H), 4.10 (t, J=6.5 Hz, 2H), 1.74 (m, 2H), 1.52-1.27 (m, 6H), 0.88 (dd, J=4.58, 9.40 Hz, 3H).

<Preparative Example 8> Preparation of 3-(2,4-bis(hexyloxy)phenyl)-2-cyanoacrylic acid

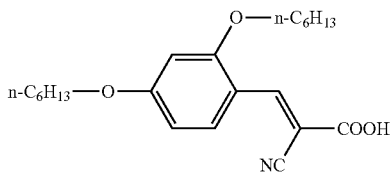

A target compound (48%) was prepared in the same manner as described in Preparative Example 4, except that 2,6-di-n-hexyloxybenzaldehyde was used instead of 4-methoxybenzaldehyde used in Preparative Example 4.

$^1$H NMR (400 MHz, CDCl$_3$) δ 8.79 (s, 1H), 8.46 (d, J=8.9 Hz, 1H), 6.58 (dd, J=9.0, 2.0 Hz, 1H), 6.42 (d, J=2.2 Hz, 2H), 4.03 (q, J=6.6 Hz, 4H), 1.83 (m, 4H), 1.55-1.28 (m, 12H), 0.92 (t, J=6.8 Hz, 6H).

<Preparative Example 9> 2-cyano-3-(3,5-dimethoxyphenyl)acrylic acid

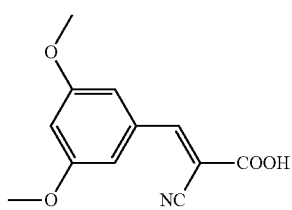 [SMILES: COc1cc(/C=C(\C#N)C(=O)O)cc(OC)c1]

A target compound (70%) was prepared in the same manner as described in Preparative Example 4, except that 3,5-dimethoxybenzaldehyde was used instead of 4-methoxybenzaldehyde used in Preparative Example 4.

$^1$H NMR (400 MHz, DMSO-d6) δ8.28 (s, 1H), 7.25 (d, J=2.1 Hz, 2H), 6.77 (t, J=2.1 Hz, 1H), 3.80 (s, 6H).

The structural formulas of the compounds prepared in Preparative Examples 1-9 are shown in Table 1 below.

TABLE 1

| | Structural Formula |
|---|---|
| Preparative Example 1 | —O—C₆H₄—C₆H₄—CH=C(CN)—COOH |
| Preparative Example 2 | CH₃CH₂—O—C₆H₄—C₆H₄—CH=C(CN)—COOH |
| Preparative Example 3 | CH₃CH₂CH₂—O—C₆H₄—C₆H₄—CH=C(CN)—COOH |
| Preparative Example 4 | CH₃—O—C₆H₄—CH=C(CN)—COOH |
| Preparative Example 5 | CH₃CH₂—O—C₆H₄—CH=C(CN)—COOH |
| Preparative Example 6 | n-C₄H₉—O—C₆H₄—CH=C(CN)—COOH |
| Preparative Example 7 | n-C₆H₁₃—O—C₆H₄—CH=C(CN)—COOH |
| Preparative Example 8 | n-C₆H₁₃—O, O—n-C₆H₁₃ substituted C₆H₃—CH=C(CN)—COOH |
| Preparative Example 9 | CH₃—O, O—CH₃ substituted C₆H₃—CH=C(CN)—COOH |

<Example> Preparation of Organic Solar Cells and Organic Photodiodes Using Cathode Buffer Material In order to evaluate the performance of an organic solar cell and an organic photodiode to which the compounds for cathode buffer material of Preparative Examples 1-9 with a large dipole moment are applied, the compounds of Preparative Examples 1-9 were applied to an organic solar cell and an organic photodiode device in which in which a photoactive layer was formed with the representative polymer donors:acceptors, PV-D4610:PC70BM, PTB7-Th:PC70BM, and PPDT2FBT:PC70BM, known to have higher energy conversion efficiency, and compared and analyzed.

<Example 1> Organic Solar Cell Using the Buffer Material of Preparative Example 1

In order to prepare an organic solar cell device to which the compound of Preparative Example 1 was applied as a buffer material, a ZnO layer was formed to a thickness of 30 nm on an ITO (Indium Tin Oxide) glass using a ZnO sol-gel solution dissolved in alcohol. Between the ZnO layer and the photoactive layer, the compound of Preparative Example 1 dissolved in a THF solvent (0.05 weight %) was spin-coated at 4000 rpm for 30 seconds. Subsequently, PV-D4610:PC70BM (1:2) (J. Mater. Chem. C, 2014, 2, 1290), known to have excellent long-term stability and easy printing process as a photoactive layer, was dissolved in benzene at the concentration of 12 mg/mL based on a polymer donor, which was spin-coated at 500 rpm for 60 seconds to form a thin film having a thickness of about 200 nm. Then, an organic solar cell device was prepared by sequentially depositing MoO₃/Ag at the thickness of 7 nm and 120 nm, respectively, in a vacuum evaporator having a vacuum degree of $3 \times 10^{-6}$ torr or less.

<Example 2> Organic Solar Cell Using the Buffer Material of Preparative Example 2

An organic solar cell device was prepared in the same manner as described in Example 1, except that the compound of Preparative Example 2 was used instead of the compound of Preparative Example 1 used in Example 1.

<Example 3> Organic Solar Cell Using the Buffer Material of Preparative Example 3

An organic solar cell device was prepared in the same manner as described in Example 1, except that the compound of Preparative Example 3 was used instead of the compound of Preparative Example 1 used in Example 1.

<Example 4> Organic Solar Cell Using the Buffer Material of Preparative Example 4

An organic solar cell device was prepared in the same manner as described in Example 1, except that the compound of Preparative Example 4 was used instead of the compound of Preparative Example 1 used in Example 1.

<Example 5> Organic Solar Cell Using the Buffer Material of Preparative Example 5

An organic solar cell device was prepared in the same manner as described in Example 1, except that the compound of Preparative Example 5 was used instead of the compound of Preparative Example 1 used in Example 1.

<Example 6> Organic Solar Cell Using the Buffer Material of Preparative Example 6

An organic solar cell device was prepared in the same manner as described in Example 1, except that the compound of Preparative Example 6 was used instead of the compound of Preparative Example 1 used in Example 1.

<Example 7> Organic Solar Cell Using the Buffer Material of Preparative Example 6-2

An organic solar cell device was prepared in the same manner as described in Example 6, except that the photoactive layer PTB7-Th:PC70BM (1:1.5) (Adv. Funct. Mater. 2016, 26, 6635), known to have higher energy conversion efficiency, instead of PV-D4610:PC70BM (1:2) used in Example 1 was dissolved in chlorobenzene at the concentration of 12 mg/mL based on a polymer donor, and DIO (Diiodooctane) was added at the concentration of 3 volume % as an additive to form a thin film having a thickness of about 100 nm.

<Example 8> Organic Solar Cell Using the Buffer Material of Preparative Example 6-3

An organic solar cell device was prepared in the same manner as described in Example 6, except that the photoactive layer PPDT2FBT:PC70BM (1:1.5) (Energy Environ. Sci., 2014, 7, 3040), known to have higher energy conversion efficiency, instead of PV-D4610:PC70BM (1:2) used in Example 1 was dissolved in chlorobenzene at the concentration of 10 mg/mL based on a polymer donor, and DPE (Diphenylether) was added at the concentration of 2 volume % as an additive to form a thin film having a thickness of about 120 nm.

<Example 9> Organic Solar Cell Using the Buffer Material of Preparative Example 6-4

First, a 30 nm thin film was spin-coated between the ITO (Indium Tin Oxide) layer and the photoactive layer using a ZnO sol-gel solution in which the compound of Preparative Example 6 was mixed at the concentration of 0.05 wt %. PV-D4610:PC70BM (1:2) as a photoactive layer was dissolved in dichlorobenzene at the concentration of 12 mg/mL based on a polymer donor, which was spin-coated at 500 rpm for 60 seconds to form a thin film having a thickness of about 200 nm. Then, an organic solar cell device was prepared by sequentially depositing $MoO_3$/Ag at the thickness of 7 nm and 120 nm, respectively, in a vacuum evaporator having a vacuum degree of $3\times10^{-6}$ torr or less.

<Example 10> Organic Solar Cell Using the Buffer Material of Preparative Example 6-5

In order to prepare a large area organic solar cell device to which the compound of Preparative Example 6 was applied as a buffer material by slot die coating, a ZnO layer was formed to a thickness of 30 nm on an ITO (Indium Tin Oxide) glass using a ZnO sol-gel solution in which the compound of Preparative Example 6 was mixed at the concentration of 0.05 wt % with a slot die coater. PV-D4610:PC70BM (1:2) used in Example 1 was dissolved in a mixed solvent of dichlorobenzene (0.8 mL) and chlorobenzone (0.2 mL) at the concentration of 14 mg/mL based on a polymer donor, and a thin film having a thickness of about 200 nm was formed using a die coater. Then, a large area organic solar cell device with a stripe pattern having a photoactive area of 60 cm$^2$ was prepared by sequentially depositing $MoO_3$/Ag at the thickness of 7 nm and 120 nm, respectively, in a vacuum evaporator having a vacuum degree of $3\times10^{-6}$ torr or less.

<Example 11> Organic Photodiode Using the Buffer Material of Preparative Example 6

In order to prepare an organic photodiode device to which the compound of Preparative Example 6 was applied as a buffer material, a ZnO layer was formed to a thickness of 30 nm on an ITO (Indium Tin Oxide) glass using a ZnO sol-gel solution dissolved in alcohol. Between the ZnO layer and the photoactive layer, the compound of Preparative Example 6 dissolved in a THF solvent (0.05 weight %) was spin-coated at 4000 rpm for 30 seconds. Subsequently, PPDT2FBT: PC70BM (1:1.5) (Energy Environ. Sci., 2014, 7, 3040) as a photoactive layer was dissolved in chlorobenzene at the concentration of 12 mg/mL based on a polymer donor, which was spin-coated at 600 rpm for 60 seconds to form a thin film having a thickness of about 120 nm. Then, an organic photodiode device was prepared by sequentially depositing $MoO_3$/Ag at the thickness of 7 nm and 120 nm, respectively, in a vacuum evaporator having a vacuum degree of $3\times10^{-6}$ torr or less.

<Example 12> Colloidal Quantum Dot Solar Cell Using the Buffer Material of Preparative Example 1

In order to prepare a quantum dot solar cell device to which the compound of Preparative Example 1 was applied as a buffer material, a ZnO layer was formed to a thickness of 40 nm on an ITO (Indium Tin Oxide) glass using a ZnO sol-gel solution dissolved in alcohol. Between the ZnO layer and the perovskite photoactive layer, the compound of Preparative Example 1 dissolved in a THF solvent (0.05 weight %) was spin-coated at 4000 rpm for 30 seconds. Subsequently, 30 uL of colloidal PbS treated with PDMII (1-propyl-2,3-dimethylimidazolium iodide) as a photoactive layer was spin-coated at 2000 rpm for 10 seconds, and 8 mg/mL of PDMII methanol solution was applied through solid-state exchange (SSE). The LBL (layer by layer) process was repeated to form a quantum dot photoactive layer having a thickness of about 270 nm, and colloidal PbS (70 nm) substituted with PDT (p-type 1,3-propanedithiol) was formed as a hole extraction layer. Then, a colloidal quantum dot solar cell device was prepared by depositing Au at the thickness of 100 nm in a vacuum evaporator having a vacuum degree of $3\times10^{-6}$ torr or less.

<Example 13> Colloidal Quantum Dot Solar Cell Using the Buffer Material of Preparative Example 4

A colloidal quantum dot solar cell device was prepared in the same manner as described in Example 12, except that the compound for a buffer material of Preparative Example 4 of the present invention was used.

<Example 14> Colloidal Quantum Dot Solar Cell Using the Buffer Material of Preparative Example 8

A colloidal quantum dot solar cell device was prepared in the same manner as described in Example 12, except that the compound for a buffer material of Preparative Example 8 of the present invention was used.

<Example 15> Perovskite Solar Cell Using the Buffer Material of Preparative Example 8

In order to prepare a perovskite solar cell device to which the compound of Preparative Example 1 was applied as a buffer material, a ZnO layer was formed to a thickness of 40 nm on an ITO (Indium Tin Oxide) glass using a ZnO sol-gel solution dissolved in alcohol. Between the ZnO layer and the perovskite photoactive layer, the compound of Preparative Example 8 dissolved in a THF solvent (0.05 weight %) was spin-coated at 4000 rpm for 30 seconds. Subsequently, PbI2:DMSO (dimethyl sulfoxide) (1:1 molarity) as a photoactive layer was dissolved in DMF (dimethyl formamide), which was spin-coated at 3000 rpm for 20 seconds, and heat-treated at 100° C. for 3 minutes to obtain a $PbI_2$ thin film. After lowering the temperature to room temperature, the film was immersed in 2-propanol containing 0.25 M methylammonium iodide (MAI) for 1 minute, and then the excess MAI was removed by immersing in 2-propanol for about 1 minute. Then, heat treatment was performed at 100° C. for 10 minutes to obtain a perovskite photoactive layer. After cooling to room temperature, spiro-OMeTAD was spin-coated to form a hole extraction layer. Then, a quantum dot solar cell was prepared by depositing Au at the thickness of 100 nm in a vacuum evaporator having a vacuum degree of $3\times10^{-6}$ torr or less.

<Comparative Example 1> Organic Solar Cell without Cathode Buffer Material

An organic solar cell device was prepared in the same manner as described in Example 1, except that the compound for a buffer material of Preparative Example of the present invention was not used.

<Comparative Example 2> Organic Solar Cell without Cathode Buffer Material 2

An organic solar cell device was prepared in the same manner as described in Comparative Example 1, except that the photoactive layer PTB7-Th:PC70BM (Adv. Funct. Mater. 2016, 26, 6635), known to have higher energy conversion efficiency, was used instead of PV-D4610: PC70BM (1:1.5) used in Comparative Example 1.

<Comparative Example 3> Organic Solar Cell without Cathode Buffer Material 3

An organic solar cell device was prepared in the same manner as described in Comparative Example 1, except that the photoactive layer PPDT2FBT:PC70BM (Energy Environ. Sci., 2014, 7, 3040), known to have higher energy conversion efficiency, was used instead of PV-D4610: PC70BM (1:2) used in Comparative Example 1.

<Comparative Example 4> Organic Solar Cell without Cathode Buffer Material 4

A large-area organic solar cell device was prepared in the same manner as described in Example 10, except that the compound for a buffer material of Preparative Example of the present invention was not used.

<Comparative Example 5> Organic Photodiode without Cathode Buffer Material

An organic photodiode device was prepared in the same manner as described in Example 11, except that the compound for a buffer material of Preparative Example of the present invention was not used.

<Comparative Example 6> Quantum Dot Solar Cell without Cathode Buffer Material

A quantum dot solar cell device was prepared in the same manner as described in Example 12, except that the compound for a buffer material of Preparative Example of the present invention was not used.

<Comparative Example 7> Perovskite Solar Cell without Cathode Buffer Material

A perovskite solar cell device was prepared in the same manner as described in Example 15, except that the compound for a buffer material of Preparative Example of the present invention was not used.

The devices prepared in Examples 1-15 and Comparative Examples 1-7 are shown in Table 2 below.

TABLE 2

|  | Device | Photoactive layer | Cathode buffer layer |
| --- | --- | --- | --- |
| Example 1 | Organic solar cell | PV-D4610:PC70BM | ZnO/Preparative Example 1 double layer |
| Example 2 | Organic solar cell | PV-D4610:PC70BM | ZnO/Preparative Example 2 double layer |
| Example 3 | Organic solar cell | PV-D4610:PC70BM | ZnO/Preparative Example 3 double layer |
| Example 4 | Organic solar cell | PV-D4610:PC70BM | ZnO/Preparative Example 4 double layer |
| Example 5 | Organic solar cell | PV-D4610:PC70BM | ZnO/Preparative Example 5 double layer |
| Example 6 | Organic solar cell | PV-D4610:PC70BM | ZnO/Preparative Example 6 double layer |
| Example 7 | Organic solar cell | PTB7-Th:PC70BM | ZnO/Preparative Example 6 double layer |
| Example 8 | Organic solar cell | PPDT2FBT:PC70BM | ZnO/Preparative Example 6 double layer |
| Example 9 | Organic solar cell | PV-D4610:PC70BM | ZnO + Preparative Example 6 mixed layer |
| Example 10 | Organic solar cell | PV-D4610:PC70BM | ZnO + Preparative Example 6 mixed layer |
| Example 11 | Organic photodiode | PPDT2FBT:PC70BM | ZnO/Preparative Example 6 double layer |

TABLE 2-continued

| Device | Photoactive layer | Cathode buffer layer |
|---|---|---|
| Example 12 | Quantum dot solar cell | PbS-PDMII:PbS-PDT | ZnO/Preparative Example 1 double layer |
| Example 13 | Quantum dot solar cell | PbS-PDMII:PbS-PDT | ZnO/Preparative Example 4 double layer |
| Example 14 | Quantum dot solar cell | PbS-PDMII:PbS-PDT | ZnO/Preparative Example 8 double layer |
| Example 15 | Perovskite solar cell | Perovskite | ZnO/Preparative Example 8 double layer |
| Comparative Example 1 | Organic solar cell | PV-D4610:PC70BM | ZnO alone |
| Comparative Example 2 | Organic solar cell | PTB7-Th:PC70BM | ZnO alone |
| Comparative Example 3 | Organic solar cell | PPDT2FBT:PC70BM | ZnO alone |
| Comparative Example 4 | Organic solar cell | PV-D4610:PC70BM | ZnO alone |
| Comparative Example 5 | Organic photodiode | PPDT2FBT:PC70BM | ZnO alone |
| Comparative Example 6 | Quantum dot solar cell | PbS-PDMII:PbS-PDT | ZnO alone |
| Comparative Example 7 | Perovskite solar cell | Perovskite | ZnO alone |

<Experimental Example 1> Evaluation of Optical and Electrochemical Properties

In order to evaluate the optical and electrochemical properties of the compounds of Preparative Examples 1-9 of the present invention, experiments were performed as follows.

First, the UV/Vis absorption spectra of the compounds of Preparation Examples 1-9 were measured to evaluate the optical properties in THF, and the results are shown in Table 3 and FIG. 1.

At this time, the absorption spectra were measured with a SHIMADZU/UV-2550 model UV-visible spectrophotometer.

Meanwhile, in order to evaluate the electrochemical properties of the compounds of Preparation Examples 1-9, the electrochemical properties were measured through CV (Cyclic Voltammetry) by dissolving in THF and using a Pt wire electrode in a solution. The results are shown in Table 3 and FIG. 2.

At this time, all the measurements were corrected to the internal standard of ferrocene (Fc), and the ionization potential (IP) value was −4.8 eV for the Fc/Fc+ redox system.

TABLE 3

| | Optical properties | | | Electrochemical properties | |
|---|---|---|---|---|---|
| Preparative Example | $^a\lambda_{max}$ (nm) | $^a\lambda_{onset}$ (nm) | $^b$Eg$_{opt}$ (eV) | $^c$Eox(V)/ $^d$HOMO (eV) | $^e$LUMO (eV) |
| 1 | 356 | 410 | 3.02 | 1.01/−5.65 | −2.63 |
| 2 | 352 | 409 | 3.03 | 1.06/−5.70 | −2.67 |
| 3 | 352 | 409 | 3.03 | 1.08/−5.72 | −2.69 |
| 4 | 335 | 373 | 3.32 | 0.77/−5.41 | −2.09 |
| 5 | 335 | 376 | 3.30 | 0.84/−5.48 | −2.18 |
| 6 | 335 | 376 | 3.30 | 0.85/−5.49 | −2.19 |
| 7 | 350 | 388 | 3.20 | 0.88/−5.59 | −2.39 |
| 8 | 378 | 416 | 2.98 | 0.97/−5.68 | −2.70 |
| 9 | 340 | 380 | 3.26 | 0.92/−5.62 | −2.36 |

($^a$dilute polymer solution in tetrahydrofuran (THF);
$^b$optical bandgap, Egopt = 1240/λonset, film;
$^c$potential determined by cyclic voltammetry with 0.1M acetonitrile and tetrabutylammonium tetrafluoroborate;
$^d$HOMO = −[4.8 + (Eoxi − EFc/Fc+)] (eV); and
$^e$LUMO = Egopt + HOMO.)

As shown in Table 3 and FIG. 1, it was confirmed that the compounds of Preparation Examples 1-9 of the present invention are advantageous compounds for obtaining a higher photocurrent since the compounds absorb light in the deep blue and ultraviolet regions to reduce absorption in the region absorbed by the photoactive layer.

Figure 2:
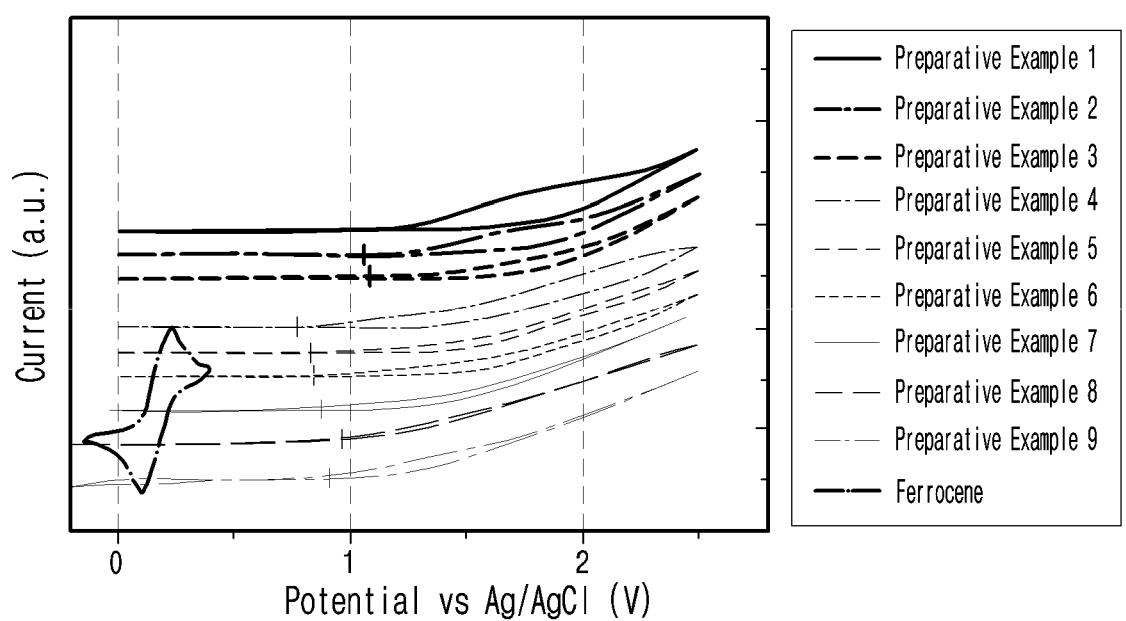
FIG. 2 is a graph showing the CV (Cyclic Voltammetry) of the compounds of Preparative Examples 1-9.

As shown in Table 3 and FIG. 2, the HOMO levels of the compounds of Preparation Examples 1-9 showed a deep value of −5.41 to −5.72 eV, and the LUMO levels obtained through the optical bandgap using the UV/Vis absorption spectra were also high.

<Experimental Example 2> Evaluation of Cathode Buffer Layer Performance

By measuring the improvement effect of the cathode buffer material using the compounds of Preparative Examples 1-6 of the present invention, for example, a ZnO layer, the performance as a cathode buffer layer was evaluated.

Particularly, in order to obtain the work function value of the sample in which the compounds of Preparative Examples 1-6 was treated on the ZnO surface, the work function of the thin film of ITO, ITO/ZnO or ITO/ZnO/Preparative Example compound was measured using UPS.

Meanwhile, each compound of Preparation Examples 1-6 was dissolved in THF at the concentration of 0.05 wt/vol % and a film was formed by spin coating on the surface of ZnO.

TABLE 4

| Thin film | B.E.(eV)$^a$ | WF(eV)$^b$ |
|---|---|---|
| ITO | 16.77 | 4.45 |
| ZnO | 17.27 | 3.95 |
| ITO/ZnO/Preparative Example 1 | 17.34 | 3.88 |
| ITO/ZnO/Preparative Example 2 | 17.62 | 3.60 |
| ITO/ZnO/Preparative Example 3 | 17.60 | 3.62 |
| ITO/ZnO/Preparative Example 4 | 17.35 | 3.85 |

TABLE 4-continued

| Thin film | B.E.(eV)[a] | WF(eV)[b] |
|---|---|---|
| ITO/ZnO/Preparative Example 5 | 17.73 | 3.47 |
| ITO/ZnO/Preparative Example 6 | 17.60 | 3.60 |

[a]B.E.(eV): binding energy(eV)
[b]WF(eV) = ΔE(21.22 eV) − B.E.(eV)

Figure 3:
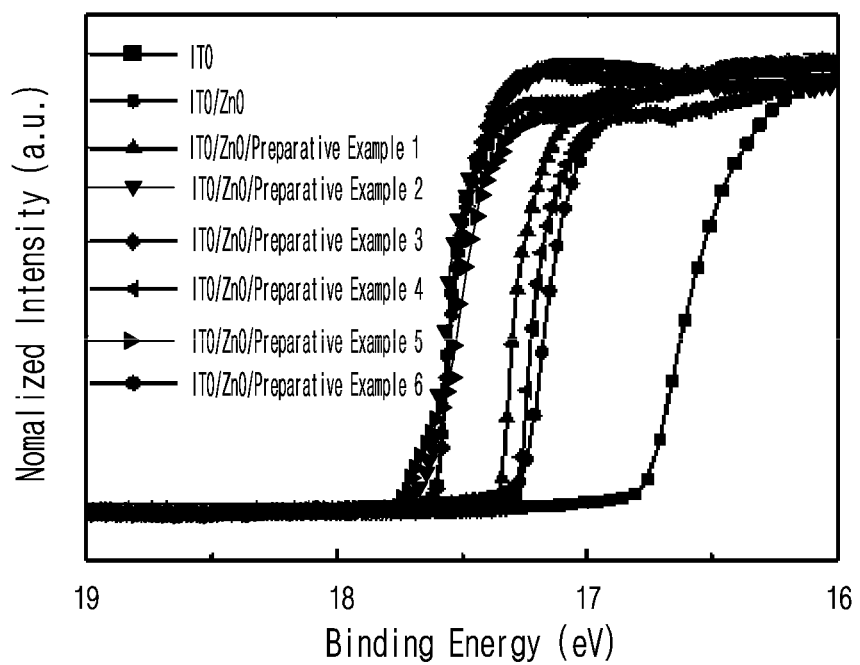
FIG. 3 is a graph showing the UPS measurement results of the layers of ITO, ITO/ZnO and ITO/ZnO/compounds of Preparative Examples 1-6.

As shown in Table 4 and FIG. 3, the work function of ITO (−4.45 eV) was changed to −3.95 eV in the condition of ITO/ZnO, and when the compound of Preparative Example 1 was stacked, it was increased to −3.88 eV. When the compounds of Preparative Example 2, Preparative Example 3, Preparative Example 4, Preparative Example 5 and Preparative Example 6 were stacked, the work functions were increased to −3.60, −3.62, −3.85, −3.47 and −3.60 eV, respectively.

From the above results, it was confirmed that the cathode buffer material of the present invention further improves the work function of the ZnO layer and contributes for improving the electron extraction characteristics of the organic electronic device.

<Experimental Example 3> Evaluation of Solar Cell Performance

Experiments were performed to evaluate the performance of the organic solar cell devices of Examples 1-10 and Comparative Examples 1-3, the colloidal quantum dot solar cells of Examples 12-14 and Comparative Example 6, and the perovskite solar cells of Example 15 and Comparative Example 7.

Particularly, each of the Voc (V) and Jsc (mA/cm²) of the organic solar cell device was obtained by calculating the voltage value when the current was 0 and the current value when the voltage was 0 in the current-voltage curve (see FIGS. 4, 5, 6 and 7) of the prepared device. In addition, FF (fill factor) was calculated according to mathematical formula 1 below.

$$FF = V_{mpp} \cdot J_{mpp} / V_{oc} \cdot J_{sc}$$ [Mathematical Formula 1]

(In mathematical formula 1, $V_{mpp}$ and $J_{mpp}$ represent the voltage and current values at the point where the maximum power factor is displayed when measuring the current-voltage of the prepared device, respectively. $V_{oc}$ (V) and $J_{sc}$ (mA/cm²) represent the voltage value when the current is 0 and the current value when the voltage is 0 in the current-voltage curve of the prepared device, respectively.)

Further, the photoelectric conversion efficiency (%) was calculated according to mathematical formula 2 below.

$$PCE(\text{photoelectric conversion efficiency, \%}) = 100 \times FF \times V_{oc} \cdot J_{sc} / P_{in}$$ [Mathematical Formula 2]

(In mathematical formula 2,

FF, $V_{oc}$ and $J_{sc}$ are as defined in mathematical formula 1, $P_{in}$ represents the total energy of light incident on the device.)

The measured values of the devices of Examples 1-10, 12-15, Comparative Examples 1-4 and 6-7 are shown in Table 5 and FIGS. 4, 5, 6, 7, 10 and 11.

TABLE 5

| | Photoactive layer | cathode buffer layer | Photoactive area (cm²) | $V_{oc}$ (V) | $J_{sc}$ (mA/cm²) | FF (%) | PCE (%) |
|---|---|---|---|---|---|---|---|
| Example 1 | PV-D4610:PC70BM | ZnO/Preparative Example 1 double layer | 0.09 | 0.80 | 16.47 | 70.81 | 9.31 |
| Example 2 | PV-D4610:PC70BM | ZnO/Preparative Example 2 double layer | 0.09 | 0.80 | 16.21 | 70.89 | 9.17 |
| Example 3 | PV-D4610:PC70B | ZnO/Preparative Example 3 double layer | 0.09 | 0.80 | 16.52 | 68.02 | 8.98 |
| Example 4 | PV-D4610:PC70BM | ZnO/Preparative Example 4 double layer | 0.09 | 0.80 | 15.74 | 73.67 | 9.26 |
| Example 5 | PV-D4610:PC70BM | ZnO/Preparative Example 5 double layer | 0.09 | 0.79 | 15.76 | 73.87 | 9.23 |
| Example 6 | PV-D4610:PC70BM | ZnO/Preparative Example 6 double layer | 0.09 | 0.79 | 16.40 | 73.41 | 9.53 |
| Example 7 | PTB7-Th:PC70BM | ZnO/Preparative Example 6 double layer | 0.09 | 0.80 | 16.21 | 68.14 | 8.81 |
| Example 8 | PPDT2FBT:PC70BM | ZnO/Preparative Example 6 double layer | 0.09 | 0.78 | 17.59 | 70.49 | 9.68 |
| Example 9 | PV-D4610:PC70BM | ZnO + Preparative Example 6 mixed layer | 0.09 | 0.79 | 16.29 | 71.53 | 9.24 |
| Example 10 | PV-D4610:PC70BM | ZnO + Preparative Example 6 mixed layer | 60 | 8.09 | 1.25 | 56.89 | 5.74 |
| Example 12 | PbS-PDMII:PbS-PDT | ZnO/Preparative Example 1 double layer | 0.09 | 0.67 | 23.0 | 64.5 | 10.01 |

TABLE 5-continued

|  | Photoactive layer | cathode buffer layer | Photoactive area (cm²) | $V_{oc}$ (V) | $J_{sc}$ (mA/cm²) | FF (%) | PCE (%) |
|---|---|---|---|---|---|---|---|
| Example 13 | PbS-PDMII:PbS-PDT | ZnO/Preparative Example 4 double layer | 0.09 | 0.68 | 23.7 | 64.8 | 10.43 |
| Example 14 | PbS-PDMII:PbS-PDT | ZnO/Preparative Example 8 double layer | 0.09 | 0.69 | 24.3 | 65.1 | 10.89 |
| Example 15 | Perovskite | ZnO/Preparative Example 8 double layer | 0.09 | 1.13 | 21.72 | 76.2 | 18.82 |
| Comparative Example 1 | PV-D4610:PC70BM | ZnO alone | 0.09 | 0.79 | 15.73 | 67.75 | 8.40 |
| Comparative Example 2 | PTB7-Th:PC70BM | ZnO alone | 0.09 | 0.79 | 15.85 | 64.44 | 8.03 |
| Comparative Example 3 | PPDT2FBT:PC70BM | ZnO alone | 0.09 | 0.77 | 16.51 | 68.97 | 8.81 |
| Comparative Example 4 | PV-D4610:PC70BM | ZnO alone | 60 | 7.7 | 1.21 | 52.71 | 4.95 |

Figure 4:
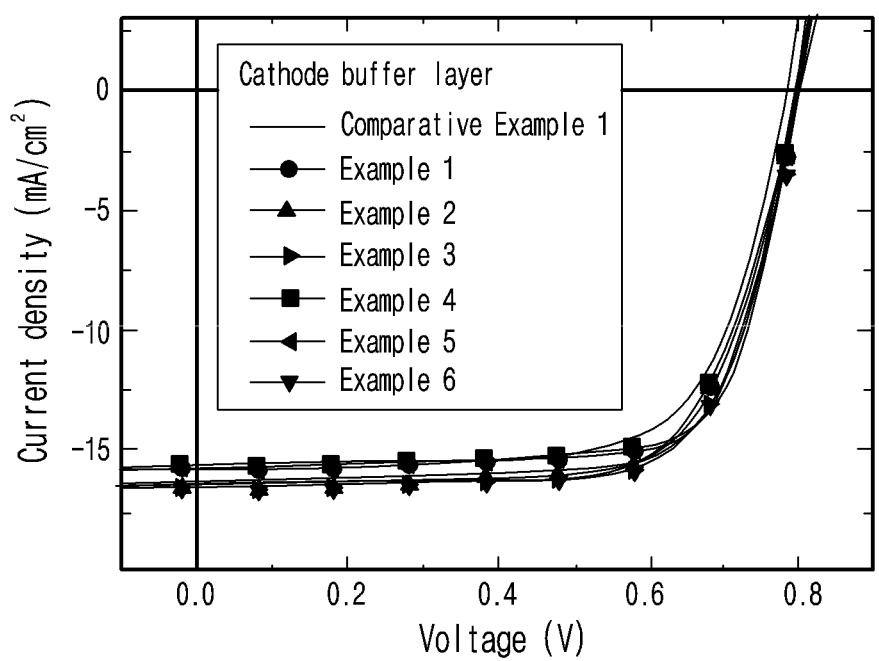
FIG. 4 is a graph showing the current density ($mA/cm^2$)-voltage (V) of the devices of Examples 1-6 and the device of Experimental Example 1 to which the PV-D4610:PC70BM photoactive layer was applied.

As shown in Table 5 and FIG. 4, in the PV-D4610:PC70BM-based inverted structure organic solar cell device, it was confirmed that the devices prepared by forming the cathode buffer layer materials of Preparative Examples 1-6 of the present invention and the ZnO layer as a double layer exhibited high conversion efficiency compared to the device prepared by applying the buffer layer formed by the conventional ZnO single layer (Comparative Example 1).

In addition, even in the case of the device (Example 9) prepared by mixing the compound of Preparative Example 1 of the present invention during the preparation of the ZnO sol-gel solution, higher conversion efficiency was confirmed compared to the device prepared by applying the buffer layer formed by the conventional ZnO single layer.

Figure 5:
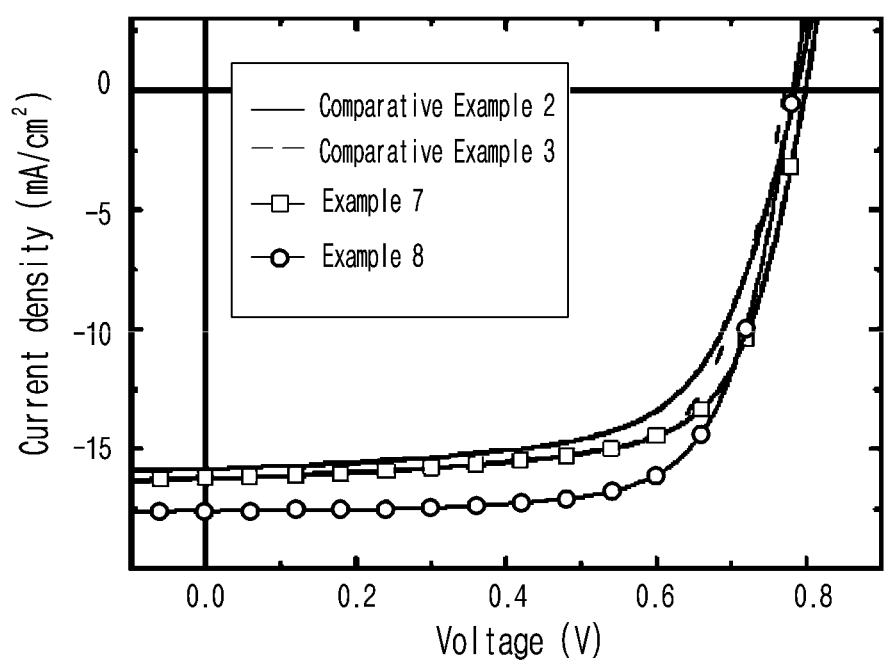
FIG. 5 is a graph showing the current density ($mA/cm^2$)-voltage (V) of the devices of Example 7 and Comparative Example 2 to which the PTB7-Th:PC70BM photoactive layer was applied, and the devices of Example 8 and Comparative Example 3 to which the PPDT2FBT:PC70BM photoactive layer was applied.

Further, as shown in FIG. 5, it was confirmed that the device of Example 8 of the present invention showed more excellent photoelectric conversion efficiency compared to the device of Comparative Example 3 even in the case of the PPDT2FBT:PC70BM based inverted structure organic solar cell device.

On the other hand, from the FF values of the devices of Examples 1-6 of the present invention, it was confirmed that the compounds of Preparative Examples 1-6 provided as a specific example in the present invention can improve the FF of an organic or organic/inorganic hybrid photoelectric device, for example, an organic solar cell, a colloidal quantum dot solar cell or a perovskite solar cell. From this, the effect of improving the energy conversion efficiency and the effect of improving the device stability from improving the shunt resistance of the device can be achieved.

Figure 6:
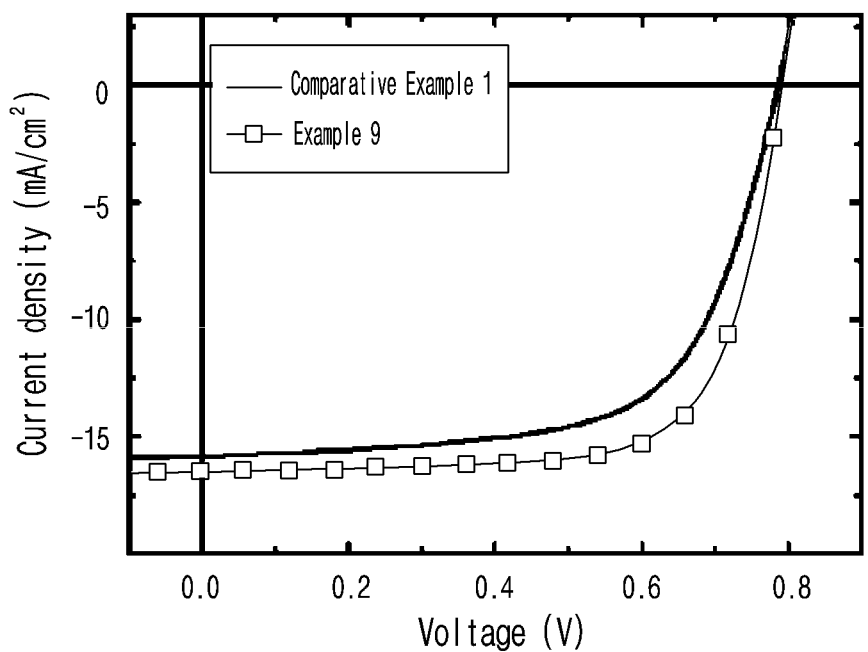
FIG. 6 is a graph showing the current density ($mA/cm^2$)-voltage (V) of the device of Comparative Example 1 consisting of a single layer of ZnO to which the PV-D4610:PC70BM photoactive layer was applied, and the device of Example 9 in which the compound layer of Preparative Example 6 was introduced after the ZnO layer was formed between −2V and +2V according to the change in the intensity of the light source.

On the other hand, it was confirmed that the excellent photoelectric conversion efficiency was still achieved even when the cathode buffer layer was prepared as a mixed single layer instead of a double layer as shown in Example 9 and FIG. 6.

Figure 7:
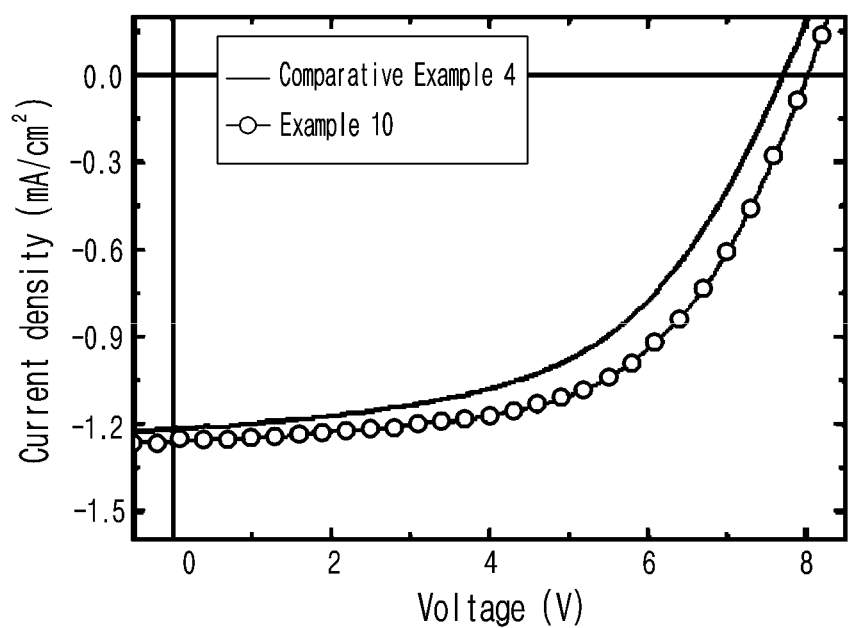
FIG. 7 is a graph showing the current density ($mA/cm^2$)-voltage (V) of the device of Comparative Example 4 consisting of a single layer of ZnO to which the PV-D4610:PC70BM photoactive layer was applied, and the device of Example 10 in which the compound layer of Preparative Example 6 was introduced after the ZnO layer was formed between −2V and +2V according to the change in the intensity of the light source.

When the cathode buffer layer was prepared as a mixed single layer, there was an advantage in that it was easy to apply the printing process, so a large-area organic solar cell with a stripe pattern having a photoactive area of 60 cm² was manufactured as shown in Example 10, which was compared with the ZnO single layer device of Comparative Example 4. As a result, as shown in FIG. 7, it was confirmed that the excellent photoelectric conversion efficiency was achieved.

From these series of results, it was confirmed that the compounds of Preparative Examples 1-8 of the present invention are industrially useful because they are easy to apply to a printing process.

Figure 10:
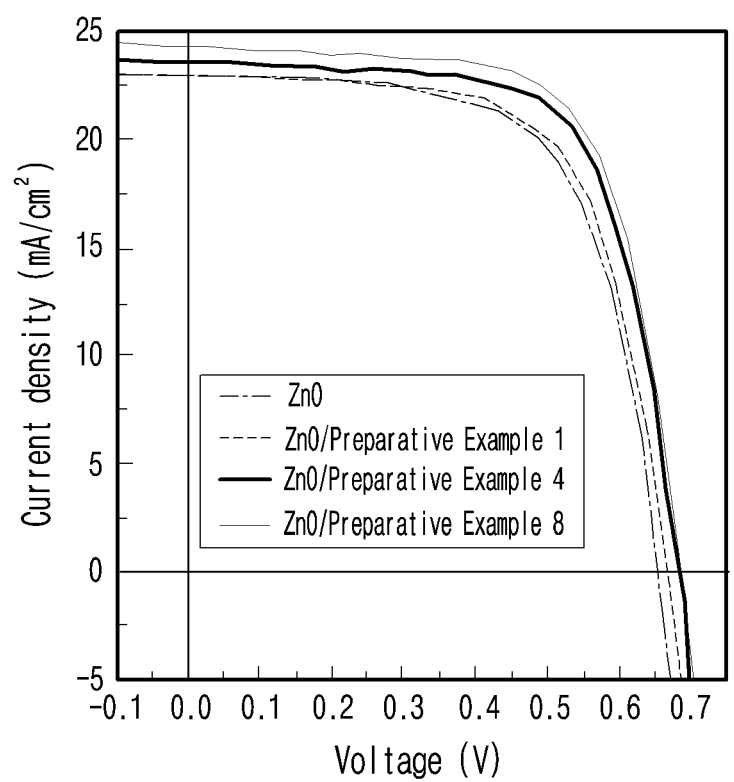
FIG. 10 is a graph showing the current density-voltage of the PbS-based colloidal quantum dot solar cells of Examples 12-14 and Comparative Example 6.

On the other hand, it was confirmed that the excellent photoelectric conversion efficiency was achieved in the colloidal quantum dot solar cell prepared as a double layer using the ZnO layer and the compounds of Preparative Examples 1, 4 and 8 as the cathode buffer layer as shown in Examples 12-14 and FIG. 10.

Figure 11A:
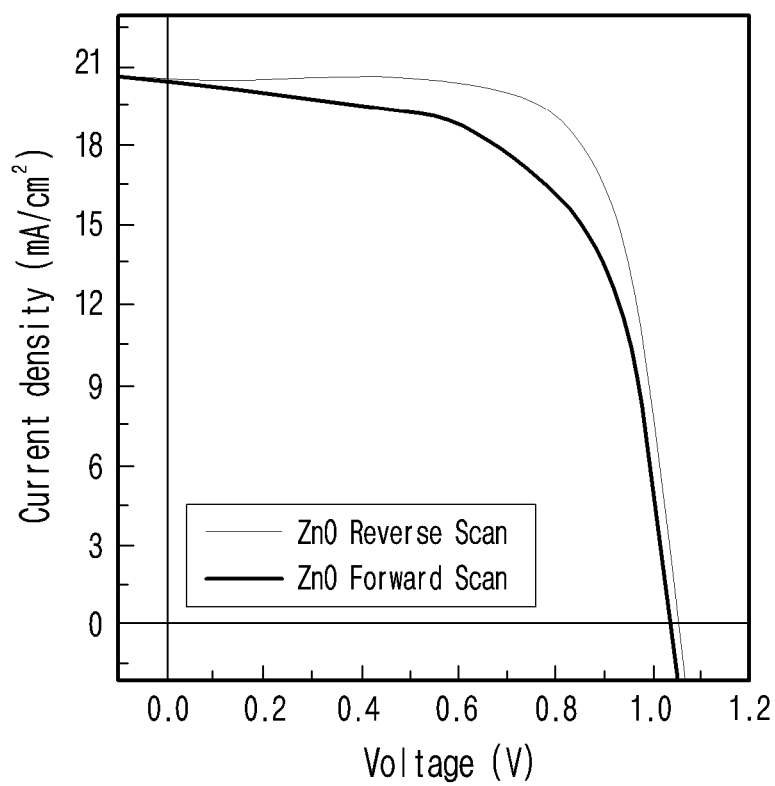
FIG. 11a is a graph showing the current density-voltage of the PbI2/MAI-based perovskite solar cell of Comparative Example 7.
Figure 11B:
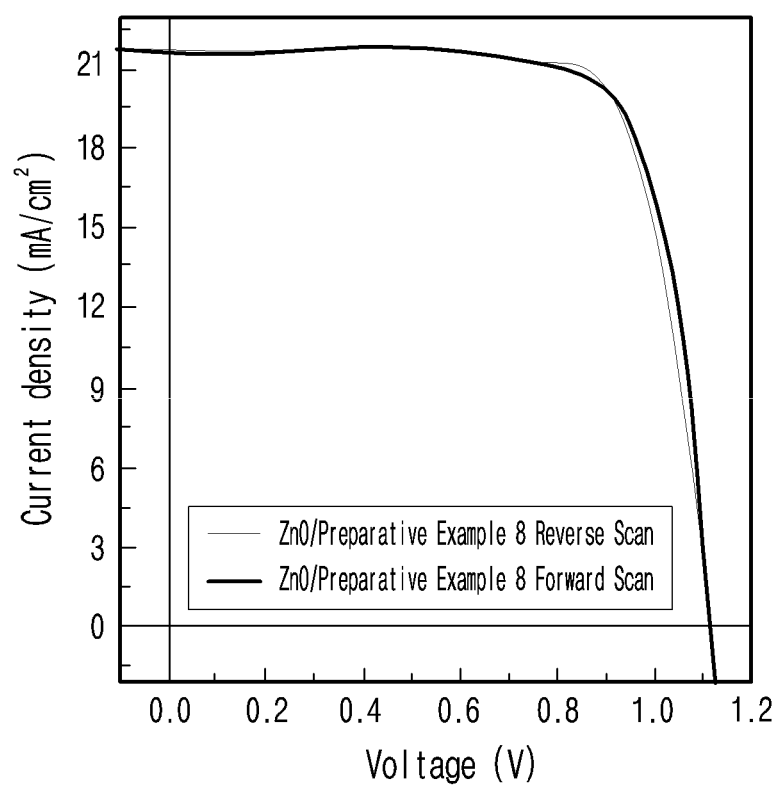
FIG. 11b is a graph showing the current density-voltage of the PbI2/MAI-based perovskite solar cell of Example 15.

As shown in Example 15 and FIG. 11b, it was also confirmed that the excellent photoelectric conversion efficiency was achieved in the perovskite solar cell prepared as a double layer using the ZnO layer and the compound of Preparative Example 8 as the cathode buffer layer. In particular, the excellence of the cathode buffer layer material of the present invention was proved through the results of a very small difference in efficiency when scanning in the reverse direction and the forward direction.

<Experimental Example 4> Evaluation of Light Detection Characteristics

Experiments were performed to evaluate the performance of the organic photodiode device of the present invention.

Particularly, photodiodes were prepared with a device structure of indium tin oxide (ITO)/ZnO/PPDT2FBT:PC70BM/MoO₃/Ag, and the photoelectric properties of the organic photodiodes of Example 11 and Comparative Example 5 were evaluated.

Figure 8:
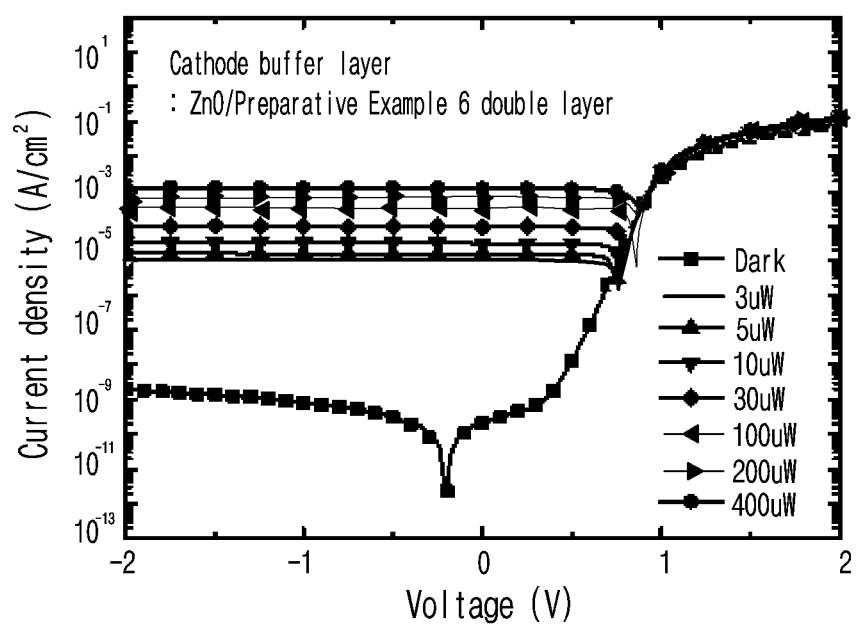
FIG. 8 is a graph showing the current density ($mA/cm^2$)-voltage (V) of a photodiode having a device structure of (ITO)/ZnO/PPDT2FBT:PC70BM/MoO$_3$/Ag using the device of Example 11 of the present invention for a capped buffer layer.
Figure 9:
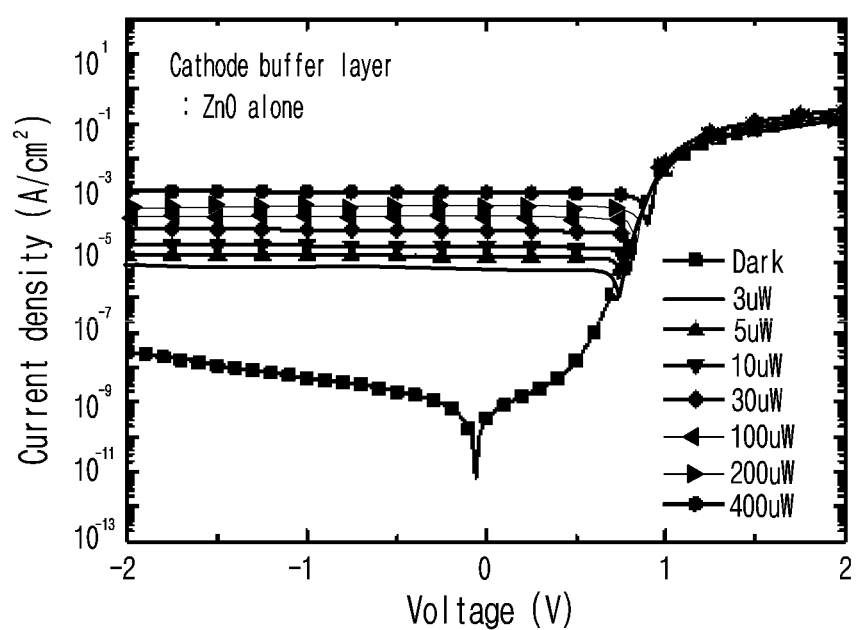
FIG. 9 is a graph showing the current density ($mA/cm^2$)-voltage (V) of a photodiode having a device structure of (ITO)/ZnO/PPDT2FBT:PC70BM/MoO3/Ag using the device of Comparative Example 5 for a capped buffer layer.

The mixing ratio of the p-type polymer and the n-type PC70BM was 1:1.5 w/w. The J-V characteristic of the device was studied in photoconduction mode because reverse bias reduces signal response time and increases signal linearity when luminosity increases. The results of the devices prepared in Example 11 and Comparative Example 5 are shown in FIGS. 8 and 9, respectively.

The responsivity and detectability of the light detecting device was obtained from the J-V characteristics as a function of voltage and light intensity, and the results of the devices prepared in Example 11 and Comparative Example 5 are summarized and shown in Tables 6 and 7, respectively.

TABLE 6

| Power | | | | At −2 V | | | | At −1 V | |
|---|---|---|---|---|---|---|---|---|---|
| | | | | Responsivity at 530 nm | Detectability at 530 nm | | | Responsivity at 530 nm | Detectability at 530 nm |
| P(μW) | P(W/cm$^2$) | JD(A/cm$^2$) | JPh(A/cm$^2$) | (A/W) | (Jones) | JD(A/cm$^2$) | JPh(A/cm$^2$) | (A/W) | (Jones) |
| 0 | 0.00E+00 | 2.84E−08 | 2.84E−08 | — | — | 4.88E−09 | 4.88E−09 | — | — |
| 30 | 3.33E−04 | 2.84E−08 | 9.09E−05 | 0.27 | 2.86E+12 | 4.88E−09 | 8.72E−05 | 0.26 | 6.62E+12 |
| 100 | 1.11E−03 | 2.84E−08 | 2.91E−04 | 0.26 | 2.75E+12 | 4.88E−09 | 2.80E−04 | 0.25 | 6.39E+12 |
| 200 | 0.002222 | 2.84E−08 | 5.84E−04 | 0.26 | 2.76E+12 | 4.88E−09 | 5.62E−04 | 0.25 | 6.41E+12 |
| 400 | 0.004444 | 2.84E−08 | 1.12E−03 | 0.25 | 2.64E+12 | 4.88E−09 | 1.08E−03 | 0.24 | 6.15E+12 |

TABLE 7

| Power | | | | At −2 V | | | | At −1 V | |
|---|---|---|---|---|---|---|---|---|---|
| | | | | Responsivity at 530 nm | Detectability at 530 nm | | | Responsivity at 530 nm | Detectability at 530 nm |
| P(μW) | P(W/cm$^2$) | JD(A/cm$^2$) | JPh(A/cm$^2$) | (A/W) | (Jones) | JD(A/cm$^2$) | JPh(A/cm$^2$) | (A/W) | (Jones) |
| 0 | 0.00E+00 | 2.84E−08 | 2.84E−08 | | | 7.88E−10 | 7.88E−10 | | |
| 30 | 3.33E−04 | 2.84E−08 | 9.09E−05 | 0.30 | 1.23E+13 | 7.88E−10 | 9.93E−05 | 0.30 | 1.88E+13 |
| 100 | 1.11E−03 | 2.84E−08 | 2.91E−04 | 0.29 | 1.18E+13 | 7.88E−10 | 3.19E−04 | 0.29 | 1.81E+13 |
| 200 | 0.002222 | 2.84E−08 | 5.84E−04 | 0.29 | 1.18E+13 | 7.88E−10 | 6.36E−04 | 0.29 | 1.80E+13 |
| 400 | 0.004444 | 2.84E−08 | 1.12E−03 | 0.29 | 1.19E+13 | 7.88E−10 | 1.27E−03 | 0.29 | 1.80E+13 |

Responsivity can be obtained simply from the output current density divided by the input optical power. As shown in FIGS. 8 and 9, the current density increased linearly as the input light intensity increased, and the device of Example 11 and the device of Comparative Example 5 were about 0.25-0.27 and 0.29-0.30 A/W, respectively, at various luminous intensity, indicating that the device to which the cathode buffer material of the present invention was applied (Example 11) was found to be better.

In conclusion, the compounds of Preparative Examples 1-9 of the present invention exhibited a very stable responsivity as a function of light intensity and driving voltage, which would be advantageous for obtaining uniform signal detection.

As shown in mathematical formula 3 below, responsivity is correlated with reactivity and dark current density ($J_d$).

$$R(\lambda) = I_{PH}/P \cdot [A/W] \quad \text{[Mathematical Formula 3]}$$

(In mathematical formula 3,
R is responsivity,
P is intensity of irradiated light,
$I_{PH}$ means generated photocurrent.)

Therefore, the responsivity means the ratio of the generated photocurrent value to the amount of the irradiated light.

On the other hand, detectivity can be obtained by mathematical formula 4 below.

$$D^* = R/(2qJ_d)^{0.5} \cdot [cm(Hz)^{1/2}/W] \quad \text{[Mathematical Formula 4]}$$

(In mathematical formula 4,
D* is detectivity,
R is responsivity of mathematical formula 3,
q is absolute quantity of electric charge, $1.6 \times 10^{-19}$ C,
$J_d$ is current density under the condition of no light (dark current density, A/cm$^2$).)

On the other hand, the response characteristic has a maximum limit because it cannot exceed the response value calculated by assuming the external quantum efficiency of 100%.

Therefore, the best way to increase the detection capability is to minimize the dark current.

As shown in Table 6 and FIG. 8, the device of Example 11 exhibited dark current densities of $4.88 \times 10^{-9}$ A/cm$^2$ and $2.84 \times 10^{-8}$ A/cm$^2$, respectively, under the conditions of applying reverse voltages of −1V and −2V. Responsivity and detectivity were calculated according to mathematical formulas 3 and 4 under the condition of applying a reverse voltage of −2V, and as a result, the responsivity and detectivity were 0.27 A/W and $2.86 \times 10^{12}$ Jones, respectively.

On the other hand, as shown in Table 7 and FIG. 9, the device of Comparative Example 5 exhibited dark current densities of $7.88 \times 10^{-10}$ A/cm$^2$ and $1.90 \times 10^{-9}$ A/cm$^2$, respectively, under the conditions of applying reverse voltages of −1V and −2V, and thus had a value 10 times higher than that of the device of Example 11. Responsivity and detectivity were calculated according to mathematical formulas 3 and 4 under the condition of applying a reverse voltage of −2V, and as a result, the responsivity and detectivity were 0.30 A/W and $1.23 \times 10^{13}$ Jones, respectively. Therefore, the device of Example 11 was found to be superior to the device of Comparative Example 5.

As described above, it was confirmed that the organic photodiode device applied with the cathode buffer material of the present invention provides lower dark current and higher photoelectric efficiency through interface control between the cathode electrode and the photoactive layer to obtain excellent responsivity and detectivity compared to the device applied with the conventional cathode buffer material, and contributes to the improvement of the performance of the organic photodiode.

In an embodiment of the present invention, in applying the compound for a cathode buffer of the present invention to an organic or organic/inorganic hybrid photoelectric device, it was found that when a film was formed as a mixed single layer may be useful in the printing process, compared to when a film was formed as a double layer.

Therefore, the compound for a cathode buffer of the present invention can be used as a cathode buffer material in organic or organic/inorganic hybrid optoelectronic devices, for example, organic solar cells, organic photodiodes, colloidal quantum dot solar cells and perovskite solar cells to improve the energy conversion efficiency of the device, minimize the leakage current, and improve the device stability by improving the shunt resistance of the device. In addition, when the compound for a cathode buffer of the present invention was applied as a double layer or as a mixed single layer, the excellent photoelectric conversion efficiency was achieved, and there was an advantage in that it was easy to apply a printing process, so that the compound of the present invention can be effectively used in industrial fields.

INDUSTRIAL APPLICABILITY

When the novel compound of the present invention is applied to cathode buffer layers of organic or organic/inorganic hybrid optoelectronic devices, for example, organic solar cells, organic photodiodes, colloidal quantum dot solar cells and perovskite solar cells, it is easy to extract electrons from the photoactive layer to the cathode electrode, and has the effect of reducing series resistance and leakage current by improving the surface characteristics of the electron transport layer through the high dipole moment of the novel compound. In addition, the compound of the present invention can significantly improve the performance of organic or organic/inorganic hybrid optoelectronic devices (organic solar cell, organic photodiode, colloidal quantum dot solar cell, perovskite solar cell, etc.), so that the compound of the present invention can be effectively used in industrial fields.

What is claimed is:

1. An organic or organic/inorganic hybrid photoelectric device comprising:
   a first electrode;
   a second electrode provided opposite to the first electrode;
   a photoactive layer provided between the first electrode and the second electrode; and
   a cathode buffer layer provided between the photoactive layer and the first electrode or the second electrode;
   wherein the photoactive layer comprises a donor comprising a polymer and an acceptor comprising fullerene; and
   wherein the cathode buffer layer comprises
      a compound according to Formula 1, or a stereoisomer thereof; and
      one or more cathode buffer materials selected from the group consisting of n-type metal oxides, transition metal chelates and alkali metal compounds,

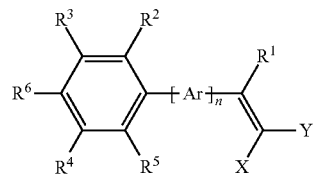

[Formula 1]

wherein with respect to Formula 1
X is $CO_2H$;
Y is CN;
Ar is substituted or unsubstituted $C_{6-10}$ arylene;
n is an integer of 0;
$R^1$ is hydrogen; and
$R^2$, $R^3$, $R^4$, $R^5$, and $R^6$ are independently H, or unsubstituted $C_{1-20}$ straight or branched alkoxy, wherein at least one of $R^2$, $R^3$, $R^4$, $R^5$, and $R^6$ is substituted or unsubstituted $C_{1-20}$ straight or branched alkoxy.

2. The organic or organic/inorganic hybrid photoelectric device according to claim 1, wherein the organic photoelectric device is an organic solar cell or an organic photodiode.

3. The organic or organic/inorganic hybrid photoelectric device according to claim 1, wherein the compound represented by Formula 1 is selected from the group consisting of the following compounds:
   (4) 2-cyano-3-(4-methoxyphenyl)acrylic acid;
   (5) 2-cyano-3-(4-ethoxyphenyl)acrylic acid;
   (6) 3-(4-butoxyphenyl)-2-cyanoacrylic acid;
   (7) 2-cyano-3-(4-(hexyloxy)phenyl)acrylic acid;
   (8) 3-(2,4-bis(hexyloxy)phenyl)-2-cyanoacrylic acid; and
   (9) 2-cyano-3-(3,5-dimethoxyphenyl)acrylic acid.

4. The organic or organic/inorganic hybrid photoelectric device according to claim 1, wherein the compound or the stereoisomer thereof is mixed and dispersed in the cathode buffer material.

5. The organic or organic/inorganic hybrid photoelectric device according to claim 1, wherein the cathode buffer layer comprises:
   a first layer comprising the cathode buffer material; and
   a second layer comprising the compound of formula 1 or the stereoisomer thereof.

* * * * *